(12) United States Patent
Custers et al.

(10) Patent No.: US 10,517,938 B2
(45) Date of Patent: Dec. 31, 2019

(54) ADENOVIRUS BASED MALARIA VACCINE ENCODING AND DISPLAYING A MALARIA ANTIGEN

(71) Applicant: Janssen Vaccines & Prevention B.V., Leiden (NL)

(72) Inventors: Jerôme H. H. V. Custers, Aphen aan den Rijn (NL); Jort Vellinga, Leiden (NL); Marija Vujadinovic, Leiden (NL); Esmerelda Van Der Helm, The Hague (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 16/071,510

(22) PCT Filed: Jan. 19, 2017

(86) PCT No.: PCT/EP2017/051029
§ 371 (c)(1),
(2) Date: Jul. 20, 2018

(87) PCT Pub. No.: WO2017/125463
PCT Pub. Date: Jul. 27, 2017

(65) Prior Publication Data
US 2019/0083597 A1  Mar. 21, 2019

(30) Foreign Application Priority Data
Jan. 21, 2016 (EP) .................................. 16152163

(51) Int. Cl.
| | | |
|---|---|---|
| A61K 39/015 | (2006.01) | |
| C12N 15/86 | (2006.01) | |
| C07K 14/005 | (2006.01) | |
| C07K 14/445 | (2006.01) | |
| A61K 39/00 | (2006.01) | |

(52) U.S. Cl.
CPC .......... *A61K 39/015* (2013.01); *C07K 14/005* (2013.01); *C07K 14/445* (2013.01); *C12N 15/86* (2013.01); *A61K 2039/5256* (2013.01); *A61K 2039/545* (2013.01); *C07K 2319/00* (2013.01); *C12N 2710/10334* (2013.01); *C12N 2710/10342* (2013.01); *Y02A 50/412* (2018.01)

(58) Field of Classification Search
CPC ............ A61K 39/015; A61K 2039/545; A61K 2039/5256; A61K 2300/00; A61K 38/00; A61K 39/12; A61K 39/00; A61K 35/761; A61K 39/235; A61K 2039/525; A61K 35/76; C07K 14/445; C07K 14/005; C07K 2319/00; C07K 2317/24; C07K 14/075; C12N 15/86; C12N 2710/10334; C12N 2710/10342; C12N 7/00; C12N 2710/10343; C12N 2710/10322; C12N 2799/021; C12N 2799/022; C12N 2710/10321; C12N 2710/10043; C12N 2710/10332; C12N 15/861; C12N 2810/6018; Y02A 50/412
See application file for complete search history.

(56) References Cited

U.S. PATENT DOCUMENTS

| | | | | |
|---|---|---|---|---|
| 2010/0272753 | A1* | 10/2010 | Ketner ................ | A61K 39/005 424/233.1 |
| 2014/0294890 | A1* | 10/2014 | Ketner ................ | A61K 39/005 424/199.1 |

FOREIGN PATENT DOCUMENTS

| | | |
|---|---|---|
| WO | 2009117656 A2 | 9/2009 |
| WO | 2011022002 A1 | 2/2011 |
| WO | 2012023995 A1 | 2/2012 |

OTHER PUBLICATIONS

Salisch NC, Vujadinovic M, van der Helm E, Spek D, Vorthoren L, Serroyen J, Kuipers H, Schuitemaker H, Zahn R, Custers J, Vellinga J. Antigen capsid-display on human adenovirus 35 via pIX fusion is a potent vaccine platform. PLoS One. Mar. 31, 2017;12(3):e0174728. eCollection 2017.*
Int'l Search Report and Written Opinion dated Mar. 10, 2017 in Int'l Application No. PCT/EP2017/051029.
Aide et al, "Four year immunogenicity of the RTS,S/AS02A malaria vaccine in Mozambican children during a phase IIb trial," Vaccine, vol. 29, pp. 6059-6067 (2011).
Alonso et al, "Duration of protection with RTS,S/AS02A malaria vaccine in prevention of Plasmodium falciparum disease in Mozambican children: single-blind extended follow-up of a randomised controlled trial," Lancet, vol. 366, pp. 2012-2018 (Dec. 10, 2005).
Alonso et al, "Efficacy of the RTS,S/AS02A vaccine against Plasmodium falciparum infection and disease in young African children:randomised controlled trial," Lancet, vol. 364, pp. 1411-1420 (Oct. 16, 2004).
Aponte et al, "Age Interactions in the Development of Naturally Acquired Immunity to Plasmodium falciparum and Its Clinical Presentation," PLos Medicine, vol. 4, No. 7, pp. 1259-1267 (Jul. 31, 2007).

(Continued)

*Primary Examiner* — Rachel B Gill
(74) *Attorney, Agent, or Firm* — Panitch Schwarze Belisario & Nadel LLP

(57) ABSTRACT

The present invention relates to novel vaccines against malaria infections, based on recombinant adenovirus vectors. Described are capsid modified replication deficient adenovirus particle encoding and displaying circumsporozoite (CS) protein NANP-repeats ($CS_{short}$) from a malaria-causing parasite, preferably *P. falciparum*, via a minor capsid protein IX and encoding a heterologous protein as a transgene. In a particular embodiment, said replication incompetent vectors of rare serotypes such as human adenovirus 35 (HAdV35) and human adenovirus 26 (HAdV26) comprise nucleic acid encoding the CS protein, as a transgene, from a malaria-causing parasite and encoding and displaying the NANP-repeat from a malaria-causing parasite (1) directly fused to the protein IX, (2) fused to protein IX via a flexible linker or (3) an alpha-helical viral origin spacer SP1 to ensure both humoral and cellular responses against the selected antigens.

16 Claims, 17 Drawing Sheets

Specification includes a Sequence Listing.

(56) References Cited

OTHER PUBLICATIONS

Bojang et al, "Efficacy of RTS,S/AS02 malaria vaccine against Plasmodium falciparum infection in semi-immune adult men in The Gambia: a randomised trial," Lancet, vol. 358, pp. 1927-1934 (Dec. 8, 2001).
Dmitriev et al, "Engineering of Adenovirus Vectors Containing Heterologous Peptide Sequences in the C Terminus of Capsid Protein IX," Journal of Virology, vol. 76, No. 14, pp. 6893-6899 (Jul. 1, 2002).
Havenga et al, "Novel replication-incompetent adenoviral B-group vectors: high vector stability and yield in PER.C6 cells," Journal of General Virology, vol. 87, pp. 2135-2143 (May 2, 2006).
Karen et al, "A Replicating Adenovirus Capsid Display Recombinant Elicits Antibodies against Plasmodium falciparum Sporozites in Aotus nancymaae Monkeys," Infection and Immunity, vol. 83, No. 1, pp. 268-275 (Jan. 16, 2015).
Kester et al, "Phase 2a trial of 0, 1, and 3 month and 0, 7, and 28 day immunization schedules of malaria vaccine RTS,S/AS02 in malaria-naïve adults at the Walter Reed Army Institute of Research," Vaccine, vol. 26, pp. 2191-2202 (2008).
Kester et al, "Efficacy of Recombinant Circumsporozoite Protein Vaccine Regimens against Experimental Plasmodium falciparum Malaria," Journal of Infectious Diseases, vol. 183, pp. 640-647 (Jan. 24, 2001).
Kester et al, "A phase I/IIa safety, immunogenicity, and efficacy bridging randomized study of a two-dose regimen of liquid and lyophilized formulations of the candidate malaria vaccine RTS,S/AS02A in malaria-naïve adults," Vaccine, vol. 25, pp. 5359-5366 (2007).
Krause et al, "Epitopes Expressed in Different Adenovirus Capsid Proteins Induce Different Levels of Epitope-Specific Immunity," Journal of Virology, vol. 80, No. 11, pp. 5523-5530 (Jun. 1, 2006).
Orphost et al, "Increased immunogenicity of recombinant Ad35-based malaria vaccine through formulation with aluminium phosphate adjuvant," Vaccine, vol. 25, pp. 6501-6510 (2007).
Palma et al, "Adenovirus particles that display the Plasmoduim falciparum circumsporozite protein NANP repeat induce sporozite-neutralizing antibodies in mice," Vaccine, vol. 29, No. 8, pp. 1683-1689 (Dec. 14, 2010).
Radosevic et al, "The Th1 Immune Response to Plasmodium falciparum Circumsporozoite Protein is Boosted by Adenovirus Vectors 35 and 26 with a Homologous Insert," Clinical and Vaccine Immunology, vol. 17, No. 11, pp. 1687-1694 (Nov. 2010).
Radosevic et al, "Protective Immune Responses to a Recombinant Adenovirus Type 35 Tuberculosis Vaccine in Two Mouse Strains: CD4 and CD8 T-cell Epitope Mapping and Role of Gamma Interferon," Infection and Immunity, vol. 75, No. 8, pp. 4105-4115 (2007).
Rodriguez et al, "Evaluation of a prime-boost vaccine schedule with distinct adenovirus vectors against malaria in rhesus monkeys," Vaccine, vol. 27, pp. 6226-6233 (2009).
Shott et al, "Adenovirus 5 and 35 vectors expressing Plasmodium falciparum circumsporozoite surface protein elicit potent antigen-specific cellular IFN-gamma and antibody responses in mice," Vaccine, No. 26, pp. 2818-2823 (2008).
Stewart et al, "Priming with an Adenovirus 35-Circumsporozoite Protein (CS) Vaccine followed by RTS,S/AS01B Boosting Significantly Improves Immunogenicity to Plasmodium falciparum CS Compared to That with Either Malaria Vaccine Alone," Infection and Immunity, vol. 75, No. 5, pp. 2283-2290 (May, 2007).
Vellinga et al, "Spacers Increase the Accessibility of Peptide Ligands Linked to the Carboxyl Terminus of Adenovirus Minor Capsid Protein IX, " Journal of Virology, vol. 78, No. 7 pp. 3470-3479 (Apr. 2004).

\* cited by examiner

| | | | | | | | |
|---|---|---|---|---|---|---|---|
| CS (TG) | KLATMMRKLA | ILSVSSFLFV | EALFQEYQCY | GSSSNTRVLN | ELNYDNAGTN | LYNELEMNYY | GKQENWYSLK 70 |
| CSshort | | | | | | | - |
| CS (TG) | KNSRSLGEND | DGNNNNGDNG | REGKDEDKRD | GNNEDNEKLR | KPKHKKKLKQP | ADGNPDPNAN | PNVDPNANPN 140 |
| CSshort | - - - - - - - - - - | - - - - - - - - - - | - - - - - - - - - - | - - - - - - - - - - | - - - - - - - - - - - | - - GNPDPNAN | PNVDPNANPN 18 |
| CS (TG) | VDPNANPNVD | VDPNANPNVD | ANPNANPNAN | ANPNANPNAN | ANPNANPNAN | PNVDPNANPN | ANPNANPNAN 210 |
| CSshort | VDPNANPNVD | VDPNANPNVD | ANPNANPNAN | ANPNANPNAN | ANPNANPNAN | PNANPNVDPN | ANPNANPNAN 88 |
| CS (TG) | PNANPNANPN | PNANPNANPN | ANPNANPNAN | ANPNANPNAN | ANPNANPNAN | PNANPNVDPN | ANPNANPNAN |
| CSshort | PNANPNANPN | PNANPNANPN | ANPNANPNAN | ANPNANPNAN | ANPNANPNAN | | |
| CS (TG) | DPNRNVDENA | NANSAVKNNN | NEEPSDKHIK | EYLNKIQNSL | STEWSPCSVT | ANPNANKNNQ | GNGQGHNMPN 280 |
| CSshort | - - - - - - - - - - | - - - - - - - - - - | - - - - - - - - - - | - - - - - - - - - - | - - - - - - - - - - | ANPNANKNNQ | GNG - - - - - 151 |
| CS (TG) | LDYANDIEKK | ICKMEKCSSY | FNVVNS 376 | | | CGNGIQVRIK | PGSANKPKDE 350 |
| CSshort | - - - - - - - - - - | - - - - - - - - - - | - - - - - - 151 | | | - - - - - - - - - - | - - - - - - - - - - 151 |

HAdV35 AdVac®

HAdV35 AdVac®

HAdV26 AdVac®

HAVd26 Advac©

HAdV35 Advac©

ADENOVIRUS BASED MALARIA VACCINE ENCODING AND DISPLAYING A MALARIA ANTIGEN

CROSS-REFERENCE TO RELATED APPLICATION

This application is a Section 371 of International Application No. PCT/EP2017/051029, filed Jan. 19, 2017, which was published in the English language on Jul. 27, 2017, under International Publication No. WO 2017/125463 A1, which claims priority under 35 U.S.C. § 119(b) to European Application No. 16152163.8, filed Jan. 21, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing", creation date of Jul. 17, 2018, and having a size of about 12 kb. The sequence listing submitted via EFS-Web is part of the specification and is herein incorporated by reference in its entirety.

FIELD OF THE INVENTION

The invention relates to the field of medicine. More in particular, the invention relates to the use of a recombinantly produced viral vector as a carrier of an antigenic determinant for the development of a vaccine against malaria infections.

BACKGROUND OF THE INVENTION

The necessity of an efficacious vaccine against the Malaria causing agent *Plasmodium falciparum* is apparent from the 800 000 deaths and over 250 million clinical cases recorded each year (WHO 2009). To reduce the disease burden and achieve complete malaria eradication in endemic countries an effective vaccine is necessary. Currently the most promising vaccine candidate, a *P. falciparum* circumsporozoite protein (CSP) based malaria vaccine termed RTS, S/AS01B/AS02A, showed promising but mixed results in clinical and field trials (1-5, 7-9). The immune correlates associated with RTS, S induced protection show a strong association between vaccine efficacy and the magnitude of the humoral and cellular responses (14).

Alternatively, Human Adenovirus (HAdV) vector expressing a circumsporozoite (CS) protein in the development of a Malaria vaccine induced high cellular responses but lower antibody responses against the CS protein (10, 11, 13). The combination of priming with HAdV35.CS and boosting with RTS,S/AS01B significantly improved immunogenicity to *P. falciparum* CS compared to either vaccine alone (15). This significant improvement of immunogenicity demonstrates the benefit of combining the HAdV vector with a strong B-cell inducer component. Hence there is a need for recombinant adenoviral vectors that induce both a strong cellular response and a strong humoral response.

DESCRIPTION OF THE INVENTION

Figure 1B:
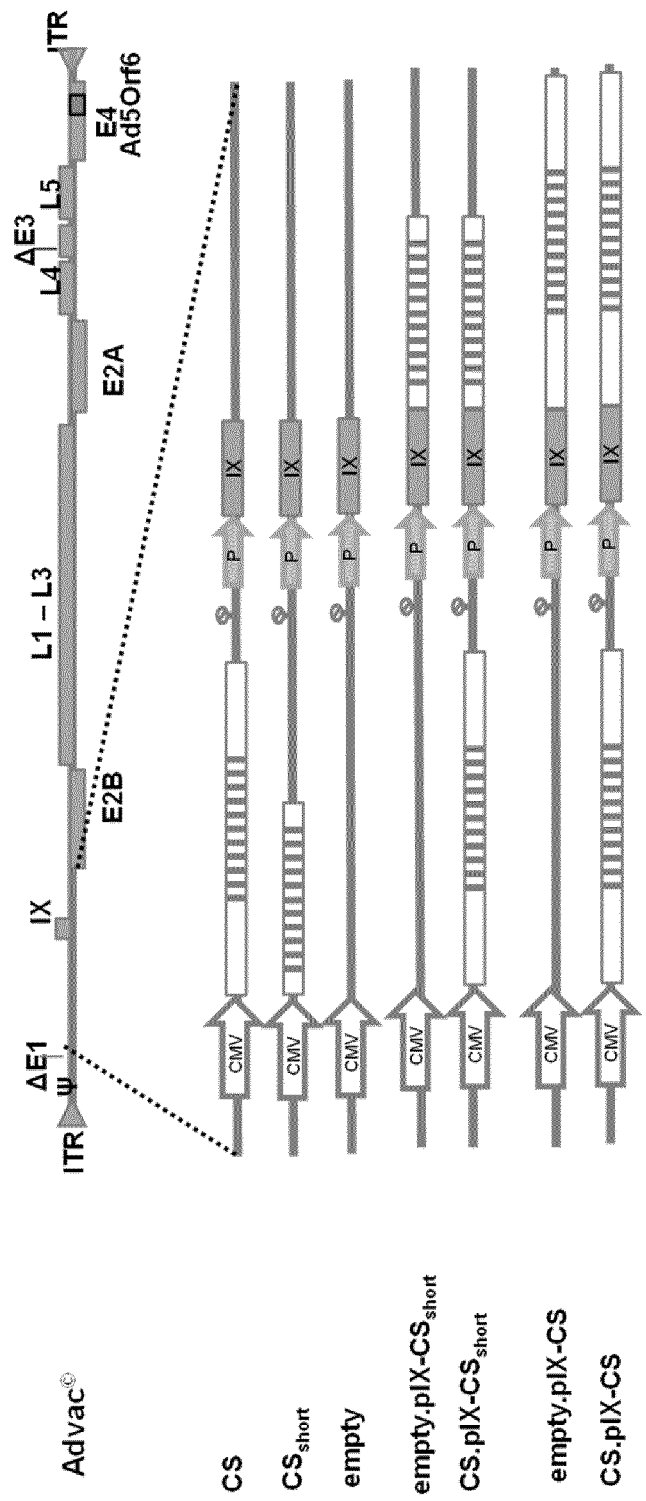
FIG. 1: Direct fusion of the $CS_{short}$ antigen to HAdV protein IX (pIX) (A) Sequence alignment of the *Plasmodium falciparum* Circumsporozoite (CS) central region with the B-cell epitope (27)NANP-repeat in the $CS_{short}$ antigen (SEQ ID NO:1) encoded and displayed on the HAdV vectors via protein IX (pIX), directly compared to the CS transgene (TG) (SEQ ID NO:8) (12) encoded in the E1 region. (B) Schematic drawing of the genetic design of HAdV vectors with an expression cassette in E1 alone and with or without encoded pIX-$CS_{short}$ and pIX-CS modification. The transgene only vectors encode CS, $CS_{short}$ or no-transgene and contain native pIX ('Empty'). pIX-$CS_{short}$ and pIX-CS modified vectors are either Empty or contain the CS transgene in E1. (C) Western Blot of viral particles to compare the capsid incorporation of the pIX-$CS_{short}$ modified vectors with or without the CS transgene and a non-modified pIX control, stained with anti-CS specific (2A10) antibody and anti-fiber (4D2) as a loading control. A serial dilution of 1.5, 0.5 and $0.17\times10^{10}$ viral particles (VP) per well are loaded and compared for the pIX-$CS_{short}$ content. Expected size of the CS transgene is ~42 kDa and pIX-$CS_{short}$ protein 32 kDa, however both proteins migrate higher in the gel due to the NANP-repeat. (D) In the left graph the depicted ELISA (EU/ml log) titers show total CS-specific (IgG) antibody responses (humoral response, B-cell response) in mice 4 weeks post immunization with $1\times10^{10}$ VP/animal of HAdV35.empty.pIX-$CS_{short}$, HAdV35.CS.pIX-$CS_{short}$ directly compared to 5 µg of CS protein and HAdV35.empty. In the right graph B-cell responses 4 weeks after immunization with 5 µg CS protein in PBS, mixed with ISCOM-based adjuvant or mixed with $1\times10^{10}$ VP/animal of empty Ad-vectors HAdV35, HAdV26, or HAdV5. Mice injected with only an adjuvant served as a control. The assay lower limit of detection (LLoC) is delineated with a dashed line. Statistical significance was determined using a two-way ANOVA test with Dunnett correction for multiple comparisons on log-transformed data. Black horizontal bars $p\leq0.05$.

The present invention relates to a recombinant adenoviral vector comprising a capsid comprising a fusion protein consisting of a protein IX and a fragment of a circumsporozoite (CS) protein of Plasmodium falciparum, wherein said fragment comprises the amino acid sequence of SEQ ID NO:1. Preferably, said fusion protein comprises a linker located in between the pIX protein and the CS protein fragment. Preferably said linker comprises an amino acid sequence having for example 2 to 15 consecutive glycine and/or serine residues.

In another embodiment according to the present invention, said fusion protein comprises a spacer, located in between the pIX protein and the CS protein fragment. Preferably, said spacer comprises the amino acid sequence of SEQ ID NO:2.(SP1). In another preferred embodiment, said spacer comprises the amino acid sequence of SEQ ID NO:3.(SP2).

In a preferred embodiment, the recombinant adenoviral vector according to the invention further comprises a nucleic acid encoding a heterologous protein. Preferably, said heterologous protein is a Malaria P. falciparum Circumsporozoite protein. Even more preferably, said Malaria P. falciparum Circumsporozoite protein comprises sequence SEQ ID NO:8.

In a preferred embodiment, the recombinant adenoviral vector according to the invention is derived from a serotype selected from the group consisting of: HAdV4, HAdV5, HAdV11, HAdV26, HAdV35, HAdV48, HAdV49 and HAdV50. Other possible types of recombinant adenoviral vectors suited for the present invention are included but not limited to: canine adenoviruses, chimp adenoviruses, gorilla adenoviruses and chimeric adenoviruses.

Preferably, said serotype is selected from the group of HAdV26, HAdV35, HAdV4, HAdV11, HAdV48 and HAdV49.

In a preferred embodiment, the recombinant adenoviral vector according to the invention is replication-defective.

The invention also relates to vaccine compositions comprising the recombinant adenoviral vector according to the invention, and a pharmaceutically acceptable carrier, further comprising preferably an adjuvant. Furthermore, the invention relates to the use of a vaccine composition according to the invention in the therapeutic, prophylactic or diagnostic treatment of malaria.

DETAILED DESCRIPTION OF THE INVENTION

The present invention relates to a replication-defective recombinant adenoviral vector comprising a capsid comprising a fusion protein consisting of a protein IX and a fragment of a circumsporozoite (CS) protein of Plasmodium falciparum. Said fragment comprises the amino acid sequence of SEQ ID NO:1.

The Malaria P. falciparum Circumsporozoite (CS) protein is a mammalian-codon CS protein optimized protein (based on EMBL CAH04007 sequence) previously described by Radosevic et al. 2011 and Rodriguez et al. 2009 (12, 13).

Two forms of the CS protein are used in the present invention. The so called "transgene" form and the so called "CS short" form (or fragment), which is a truncated form of the CS protein (FIG. 1A). The CS short comprises the amino acid sequence SEQ ID NO:1.

The transgene CS is similar to the native CS protein (3D7 clone) except for the final 14 amino acids in the C-terminus which are truncated. The transgene (TG) is inserted and encoded in the E1 region of the adenoviral vector. The repeat region of the CS protein consist of 27 consecutive NANP-repeats which are present in both transgene (TG) and the truncated form (CS$_{short}$) which is fused to protein IX. The transgene form of the CS protein comprises the amino acid sequence SEQ ID NO:8.

The term Protein IX (pIX) refers to a protein with the main function of stabilizing the icosahedral Adenovirus capsid (Rose-Calatrava et al. 2001).

The pIX is adenovirus serotype specific, i.e. the pIX in a serotype 35 Adenovirus (HAdV35) comprises the amino acid sequence SEQ ID NO:6; the pIX in a serotype 26 Adenovirus (HAdV26) comprises the amino acid sequence SEQ ID NO:7.

The term linker refers to short peptide sequences that can be placed between protein domains. Linkers are composed of flexible residues such as glycine (gly) and/or serine in different size ranges, ensuring free movement of different domains relative to one another. Examples of linkers include but are not limited to 3-Gly (Gly-Gly-Gly) and middle linker (Gly-Gly-Ser-Gly)×2. In one preferred embodiment according to the present invention, the Glycine linker comprises an amino acid sequence having 2 to 15 consecutive glycine and/or Serine residues.

The term spacer refers to short peptide sequences that can be placed between protein domains. Several spacers are disclosed herein and can be used in the present invention, i.e. the ApoE4 protein alpha-helical 45 Å spacer (16) that is from human ApoE4 protein origin; the spacer 1 (SP1), a RSV Fusion protein; the spacer 2 (SP2), an Influenza A HA; the spacer 3 (SP3), a Mumps Fusion protein and finally spacer 4 (SP4), a HAdV35.pIX fragment with point mutations. The SP1-SP4 spacers are from viral origin and comprise the amino sequences SEQ ID NO: 2, SEQ ID NO: 3, SEQ ID NO: 4 and SEQ ID NO:5 respectively.

The term 'recombinant' for an adenovirus, as used herein implicates that it has been modified by the hand of man, e.g. it has altered terminal ends actively cloned therein and/or it comprises a heterologous gene, i.e. it is not a naturally occurring wild type adenovirus.

Sequences herein are provided from 5' to 3' direction, as custom in the art.

An "adenovirus capsid protein" refers to a protein on the capsid of an adenovirus that is involved in determining the serotype and/or tropism of a particular adenovirus. Adenoviral capsid proteins typically include the fiber, penton and/or hexon proteins. An adenovirus of (or 'based upon') a certain serotype according to the invention typically comprises fiber, penton and/or hexon proteins of that certain serotype, and preferably comprises fiber, penton and hexon protein of that certain serotype. These proteins are typically encoded by the genome of the recombinant adenovirus. A recombinant adenovirus of a certain serotype may optionally comprise and/or encode other proteins from other adenovirus serotypes. Thus, as non-limiting example, a recombinant adenovirus that comprises hexon, penton and fiber of HAdV35 is considered a recombinant adenovirus based upon HAdV35.

A recombinant adenovirus is 'based upon' an adenovirus as used herein, by derivation from the wild type, at least in sequence. This can be accomplished by molecular cloning, using the wild type genome or parts thereof as starting material. It is also possible to use the known sequence of a wild type adenovirus genome to generate (parts of) the genome de novo by DNA synthesis, which can be performed using routine procedures by service companies having business in the field of DNA synthesis and/or molecular cloning (e.g. GeneArt, Invitrogen, GenScripts, Eurofins).

The recombinant adenovirus of the present invention is preferably based upon an adenovirus from a serotype selected from the group consisting of: HAdV4, HAdV5, HAdV11, HAdV26, HAdV35, HAdV48, HAdV49 and Ad50. Other possible types of adenoviruses suited for the present invention are included but not limited to: canine adenoviruses, chimp adenoviruses, gorilla adenoviruses and chimeric adenoviruses. Preferably, said serotype is selected from the group of HAdV4, HAdV26, HAdV35, HAdV48, HAdV49 and HAdV50.

The replication-defective recombinant adenoviral vector further comprises a heterologous nucleic acid encoding a heterologous antigen (or polypeptide).

It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

In one particular aspect of the invention the recombinant viral vector according to the invention, comprises a nucleic acid encoding an antigenic determinant that is the circumsporozoite (CS) protein, or an immunogenic part thereof. Preferably, said heterologous nucleic acid is codon-optimized for elevated expression in a mammal, preferably a human. Codon-optimization is based on the required amino acid content, the general optimal codon usage in the mammal of interest and a number of provisions of aspects that should be avoided to ensure proper expression. Such aspects may be splice donor or acceptor sites, stop codons, Chi-sites, poly(A) stretches, GC- and AT-rich sequences, internal TATA boxes, et cetera.

In a preferred embodiment, the invention relates to a replication-defective recombinant viral vector according to the invention, wherein the adenine plus thymine content in said heterologous nucleic acid, as compared to the cytosine plus guanine content, is less than 87%, preferably less than 80%, more preferably less than 59% and most preferably equal to approximately 45%.

The person skilled in the art will also appreciate that changes can be made to a protein, e.g. by amino acid substitutions, deletions, additions, etc, e.g. using routine molecular biology procedures. Generally, conservative amino acid substitutions may be applied without loss of function or immunogenicity of a polypeptide. This can easily be checked according to routine procedures well known to the skilled person.

The term "vaccine" refers to an agent or composition containing an active component effective to induce a therapeutic degree of immunity in a subject against a certain pathogen or disease. In the present invention, the vaccine comprises an effective amount of a recombinant adenovirus that encodes a heterologous protein, or an antigenic fragment thereof, which results in an immune response against the heterologous protein. The term "vaccine" according to the invention implies that it is a pharmaceutical composition, and thus typically includes a pharmaceutically acceptable diluent, carrier or excipient. It may or may not comprise further active ingredients. In certain embodiments it may be a combination vaccine that further comprises other components that induce an immune response, e.g. against other proteins and/or against other infectious agents.

The vectors of the present invention are recombinant adenoviruses, also referred to as recombinant adenoviral vectors. The preparation of recombinant adenoviral vectors is well known in the art.

In certain embodiments, an adenoviral vector according to the invention is deficient in at least one essential gene function of the E1 region, e.g. the E1a region and/or the E1b region, of the adenoviral genome that is required for viral replication.

In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient", meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region).

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, 6,113,913, and 8,932,607 and Thomas Shenk, "Adenoviridae and their Replication", M. S. Horwitz, "Adenoviruses", Chapters 67 and 68, respectively, in Virology, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., Molecular Cloning, a Laboratory Manual, 2d ed., Cold Spring Harbor Press, Cold Spring Harbor, N.Y. (1989), Watson et al., Recombinant DNA, 2d ed., Scientific American Books (1992), and Ausubel et al., Current Protocols in Molecular Biology, Wiley Interscience Publishers, NY (1995), and other references mentioned herein.

According to the invention, an adenovirus is a human adenovirus of the serotype 35. The vaccines according to the invention based on this serotype as well as those based on HAdV26 surprisingly appear more potent than the ones described in the prior art that were based on HAdV5. The serotype of the invention further generally has a low seroprevalence and/or low pre-existing neutralizing antibody titers in the human population. Recombinant adenoviral vectors of this serotype and of HAdV26 with different transgenes are evaluated in clinical trials, and thus far show to have an excellent safety profile. Preparation of HAdV26 vectors is described, for example, in WO 2007/104792 and in Abbink et al., (2007) Virol 81(9): 4654-63. Exemplary genome sequences of HAdV26 are found in GenBank Accession EF 153474 and in SEQ ID NO:1 of WO 2007/104792. Preparation of HAdV35 vectors is described, for example, in U.S. Pat. No. 7,270,811, in WO 00/70071, and in Vogels et al., (2003) J Virol 77(15): 8263-71. Exemplary genome sequences of HAdV35 are found in GenBank Accession AC_000019 and in FIG. 6 of WO 00/70071. A recombinant adenovirus according to the invention may be replication-competent or replication-deficient.

In certain embodiments, the adenovirus is replication deficient, e.g. because it contains a deletion in the E1 region of the genome. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as 'packaging cell' or 'complementing cell' or 'host cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al, 2000, Human Gene Therapy 11: 213-219), 293, and the like. In certain embodiments, the producer cells are for instance HEK293 cells, or PER.C6 cells, or 911 cells, or IT293SF cells, and the like.

For non-subgroup C E1-deficient adenoviruses such as HAdV35 (subgroup B) or HAdV26 (subgroup D), it is preferred to exchange the E4-orf6 coding sequence of these non-subgroup C adenoviruses with the E4-orf6 of an adenovirus of subgroup C such as HAdV5. This allows propagation of such adenoviruses in well known complementing cell lines that express the E1 genes of Ad5, such as for example 293 cells or PER.C6 cells (see, e.g. Havenga et al, 2006, J. Gen. Virol. 87: 2135-2143; WO 03/104467, incorporated in its entirety by reference herein). In certain embodiments, the adenovirus in the vaccine composition is a human adenovirus of serotype 35, with a deletion in the E1 region into which the nucleic acid encoding a CS protein antigen has been cloned, and with an E4 orf6 region of HAdV5. In certain embodiments, an adenovirus in that can be used is a human adenovirus of serotype 26, with a deletion in the E1 region into which the nucleic acid encoding a CS protein antigen has been cloned, and with an E4 orf6 region of HAdV5.

In alternative embodiments, there is no need to place a heterologous E4orf6 region (e.g. of HAdV5) in the adenoviral vector, but instead the E1-deficient non-subgroup C vector is propagated in a cell line that expresses both E1 and a compatible E4orf6, e.g. the 293-ORF6 cell line that expresses both E1 and E4orf6 from Ad5 (see e.g. Brough et al, 1996, J Virol 70: 6497-501 describing the generation of the 293-ORF6 cells; Abrahamsen et al, 1997, J Virol 71: 8946-51 and Nan et al, 2003, Gene Therapy 10: 326-36 each describing generation of E1 deleted non-subgroup C adenoviral vectors using such a cell line).

Alternatively, a complementing cell that expresses E1 from the serotype that is to be propagated can be used (see e.g. WO 00/70071, WO 02/40665).

For subgroup B adenoviruses, such as HAdV35, having a deletion in the E1 region, it is preferred to retain the 3' end of the E1B 55K open reading frame in the adenovirus, for instance the 166 bp directly upstream of the pIX open reading frame or a fragment comprising this such as a 243 bp fragment directly upstream of the pIX start codon (marked at the 5' end by a Bsu36I restriction site in the HAdV35 genome), since this increases the stability of the adenovirus because the promoter of the pIX gene is partly residing in this area (see, e.g. Havenga et al, 2006, J. Gen. Virol. 87: 2135-2143; WO 2004/001032, incorporated by reference herein).

In certain embodiments, the recombinant HAdV26 or HAdV35 vectors of the invention comprise as the 5' terminal nucleotides the nucleotide sequence: CTATCTAT. These embodiments are advantageous because such vectors display improved replication in production processes, resulting in batches of adenovirus with improved homogeneity, as compared to vectors having the original 5' terminal sequences (generally CATCATCA) (see also patent application nos. PCT/EP2013/054846 and U.S. Ser. No. 13/794, 318, entitled 'Batches of recombinant adenovirus with altered terminal ends' filed on 12 Mar. 2012 in the name of Crucell Holland B.V.), incorporated in its entirety by reference herein. The invention thus also provides batches of recombinant adenovirus encoding a CS protein or a part thereof, wherein the adenovirus is a human adenovirus serotype 35, and wherein essentially all (e.g. at least 90%) of the adenoviruses in the batch comprise a genome with terminal nucleotide sequence CTATCTAT.

The term 'about' for numerical values as used in the present disclosure means the value ±10%.

In certain embodiments, the invention provides methods for making a vaccine against Malaria or an other infections diseases antigen, i.e. Tuberculosis, comprising providing a recombinant adenoviral vector comprising a capsid comprising a fusion protein consisting of a protein IX and a fragment of a circumsporozoite (CS) protein of *Plasmodium falciparum*, wherein said fragment comprises the amino acid sequence of SEQ ID NO:1, propagating said recombinant adenovirus in a culture of host cells, isolating and purifying the recombinant adenovirus, and bringing the recombinant adenovirus in a pharmaceutically acceptable composition.

Recombinant adenovirus can be prepared and propagated in host cells, according to well known methods, which entail cell culture of the host cells that are infected with the adenovirus. The cell culture can be any type of cell culture, including adherent cell culture, e.g. cells attached to the surface of a culture vessel or to microcarriers, as well as suspension culture.

Most large-scale suspension cultures are operated as batch or fed-batch processes because they are the most straightforward to operate and scale up. Nowadays, continuous processes based on perfusion principles are becoming more common and are also suitable (see e.g. WO 2010/060719, and WO 2011/098592, both incorporated by reference herein, which describe suitable methods for obtaining and purifying large amounts of recombinant adenoviruses).

Producer cells are cultured to increase cell and virus numbers and/or virus titers. Culturing a cell is done to enable it to metabolize, and/or grow and/or divide and/or produce virus of interest according to the invention. This can be accomplished by methods as such well known to persons skilled in the art, and includes but is not limited to providing nutrients for the cell, for instance in the appropriate culture media. Suitable culture media are well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9)).

Typically, the adenovirus will be exposed to the appropriate producer cell in a culture, permitting uptake of the virus. Usually, the optimal agitation is between about 50 and 300 rpm, typically about 100-200, e.g. about 150, typical DO is 20-60%, e.g. 40%, the optimal pH is between 6.7 and 7.7, the optimal temperature between 30 and 39° C., e.g. 34-37° C., and the optimal MOI between 5 and 1000, e.g. about 50-300. Typically, adenovirus infects producer cells spontaneously, and bringing the producer cells into contact with recombinant adeviral particles is sufficient for infection of the cells. Generally, an adenovirus seed stock is added to the culture to initiate infection, and subsequently the adenovirus propagates in the producer cells. This is all routine for the person skilled in the art.

After infection of an adenovirus, the virus replicates inside the cell and is thereby amplified, a process referred to herein as propagation of adenovirus.

Adenovirus infection results finally in the lysis of the cells being infected. The lytic characteristics of adenovirus therefore permits two different modes of virus production. The first mode is harvesting virus prior to cell lysis, employing external factors to lyse the cells. The second mode is harvesting virus supernatant after (almost) complete cell lysis by the produced virus (see e.g. U.S. Pat. No. 6,485,958, describing the harvesting of adenovirus without lysis of the host cells by an external factor). It is preferred to employ external factors to actively lyse the cells for harvesting the adenovirus.

Methods that can be used for active cell lysis are known to the person skilled in the art, and have for instance been discussed in WO 98/22588, p. 28-35. Useful methods in this respect are for example, freeze-thaw, solid shear, hypertonic and/or hypotonic lysis, liquid shear, sonication, high pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents that can be used, and the way they are employed, are generally known to the person skilled in the art. Several examples are for instance discussed in WO 98/22588, p. 29-33. Detergents can include anionic, cationic, zwitterionic, and nonionic detergents. The concentration of the detergent may be varied, for instance within the range of about 0.1%-5% (w/w). In one embodiment, the detergent used is Triton X-100.

Nuclease may be employed to remove contaminating, i.e. mostly from the producer cell, nucleic acids. Exemplary nucleases suitable for use in the present invention include Benzonase®, Pulmozyme®, or any other DNase and/or RNase commonly used within the art. In preferred embodiments, the nuclease is Benzonase®, which rapidly hydrolyzes nucleic acids by hydrolyzing internal phosphodiester bonds between specific nucleotides, thereby reducing the viscosity of the cell lysate. Benzonase® can be commercially obtained from Merck KGaA (code W214950). The concentration in which the nuclease is employed is preferably within the range of 1-100 units/ml. Alternatively, or in addition to nuclease treatment, it is also possible to selectively precipitate host cell DNA away from adenovirus preparations during adenovirus purification, using selective precipitating agents such as domiphen bromide (see e.g.

U.S. Pat. No. 7,326,555; Goerke et al., 2005, Biotechnology and bioengineering, Vol. 91: 12-21; WO 2011/045378; WO 2011/045381).

Methods for harvesting adenovirus from cultures of producer cells have been extensively described in WO 2005/080556.

In certain embodiments, the harvested adenovirus is further purified. Purification of the adenovirus can be performed in several steps comprising clarification, ultrafiltration, diafiltration or separation with chromatography as described in for instance WO 05/080556, incorporated by reference herein. Clarification may be done by a filtration step, removing cell debris and other impurities from the cell lysate. Ultrafiltration is used to concentrate the virus solution. Diafiltration, or buffer exchange, using ultrafilters is a way for removal and exchange of salts, sugars and the like. The person skilled in the art knows how to find the optimal conditions for each purification step. Also WO 98/22588, incorporated in its entirety by reference herein, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Preferably, purification employs at least one chromatography step, as for instance discussed in WO 98/22588, p. 61-70. Many processes have been described for the further purification of adenoviruses, wherein chromatography steps are included in the process. The person skilled in the art will be aware of these processes, and can vary the exact way of employing chromatographic steps to optimize the process. It is for instance possible to purify adenoviruses by anion exchange chromatography steps, see for instance WO 2005/080556 and Konz et al, 2005, Hum Gene Ther 16: 1346-1353. Many other adenovirus purification methods have been described and are within the reach of the skilled person. Further methods for producing and purifying adenoviruses are disclosed in for example (WO 00/32754; WO 04/020971; U.S. Pat. Nos. 5,837,520; 6,261,823; WO 2006/108707; Konz et al, 2008, Methods Mol Biol 434: 13-23; Altaras et al, 2005, Adv Biochem Eng Biotechnol 99: 193-260), all incorporated by reference herein.

For administering to humans, the invention may employ pharmaceutical compositions comprising the Adenovirus and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The purified Ad preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g pH 5.0 to 7.5. The Ad typically is in a solution having a suitable pharmaceutically acceptable buffer, and the solution of Ad may also contain a salt. Optionally stabilizing agent may be present, such as albumin. In certain embodiments, detergent is added. In certain embodiments, Ad may be formulated into an injectable preparation. These formulations contain effective amounts of Ad, are either sterile liquid solutions, liquid suspensions or lyophilized versions and optionally contain stabilizers or excipients. An adenovirus vaccine can also be aerosolized for intranasal administration (see e.g. WO 2009/117134).

For instance, adenovirus may be stored in the buffer that is also used for the Adenovirus World Standard (Hoganson et al, Development of a stable adenoviral vector formulation, Bioprocessing March 2002, p. 43-48): 20 mM Tris pH 8, 25 mM NaCl, 2.5% glycerol. Another useful formulation buffer suitable for administration to humans is 20 mM Tris, 2 mM MgCl2, 25 mM NaCl, sucrose 10% w/v, polysorbate-80 0.02% w/v. Obviously, many other buffers can be used, and several examples of suitable formulations for the storage and for pharmaceutical administration of purified (adeno)virus preparations can for instance be found in European patent no. 0853660, U.S. Pat. No. 6,225,289 and in international patent applications WO 99/41416, WO 99/12568, WO 00/29024, WO 01/66137, WO 03/049763, WO 03/078592, WO 03/061708.

In certain embodiments a composition comprising the adenovirus further comprises one or more adjuvants. Adjuvants are known in the art to further increase the immune response to an applied antigenic determinant, and pharmaceutical compositions comprising adenovirus and suitable adjuvants are for instance disclosed in WO 2007/110409, incorporated by reference herein. The terms "adjuvant" and "immune stimulant" are used interchangeably herein, and are defined as one or more substances that cause stimulation of the immune system. In this context, an adjuvant is used to enhance an immune response to the adenovirus vectors of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, and the like. It is also possible to use vector-encoded adjuvant, e.g. by using heterologous nucleic acid that encodes a fusion of the oligomerization domain of C4-binding protein (C4bp) to the antigen of interest (e.g. Solabomi et al, 2008, Infect Immun 76: 3817-23). In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

In other embodiments, the compositions do not comprise adjuvants.

It is also possible according to the invention to administer further active components, in combination with the vaccines according to the invention. Such further active components may comprise e.g. other Malaria antigens or vectors comprising nucleic acid encoding these. Such vectors may be non-adenoviral or adenoviral, of which the latter can be of any serotype. An example of other Malaria antigens includes Malaria proteins or immunologically active parts thereof.

Further active components may also comprise non-Malaria antigens, e.g. from other pathogens such as viruses, bacteria, parasites, and the like. The administration of further active components may for instance be done by separate administration or by administering combination products of the vaccines of the invention and the further active components. In certain embodiments, further non-adenoviral antigens, may be encoded in the vectors of the invention. In certain embodiments, it may thus be desired to express more than one protein from a single adenovirus, and in such cases more coding sequences for instance may be linked to form a single transcript from a single expression cassette or may be present in two separate expression cassettes cloned in different parts of the adenoviral genome.

Adenovirus compositions may be administered to a subject, e.g. a human subject. The total dose of the adenovirus provided to a subject during one administration can be varied as is known to the skilled practitioner, and is generally between $1\times10^7$ viral particles (VP) and $1\times10^{12}$ VP, preferably between $1\times10^8$ VP and $1\times10^{11}$ VP, for instance between $3\times10^8$ and $5\times10^{19}$ VP, for instance between $10^9$ and $3\times10^{19}$ VP.

Administration of adenovirus compositions can be performed using standard routes of administration. Non-limiting embodiments include parenteral administration, such as by injection e.g. intradermal, intramuscular, etc, or subcutaneous, transcutaneous, or mucosal administration, e.g. intranasal, oral, and the like. It is preferred according to the present invention to administer the vaccine intramuscularly. The advantage of intramuscular administration is that it is simple and well-established, and does not carry the safety concerns for intranasal application in infants younger than 6 months. In one embodiment a composition is administered by intramuscular injection, e.g. into the deltoid muscle of the arm, or vastus lateralis muscle of the thigh. The skilled person knows the various possibilities to administer a composition, e.g. a vaccine in order to induce an immune response to the antigen(s) in the vaccine.

A subject as used herein preferably is a mammal, for instance a rodent, e.g. a mouse, a cotton rat, or a non-human-primate, or a human. Preferably, the subject is a human subject. The subject can be of any age, e.g. from about 1 month to 100 years old, e.g. from about 2 months to about 80 years old, e.g. from about 1 month to about 3 years old, from about 3 years to about 50 years old, from about 50 years to about 75 years old, etc.

It is also possible to provide one or more booster administrations of one or more adenovirus vaccines of the invention. If a boosting vaccination is performed, typically, such a boosting vaccination will be administered to the same subject at a moment between one week and one year, preferably between two weeks and four months, after administering the composition to the subject for the first time (which is in such cases referred to as 'priming vaccination'). In alternative boosting regimens, it is also possible to administer different vectors, e.g. one or more adenoviruses of different serotype, or other vectors such as MVA, or DNA, or protein, to the subject after the priming vaccination. It is for instance possible to administer to the subject a recombinant adenoviral vector according to the invention as a prime, and boosting with a composition comprising a malaria protein.

In certain embodiments, the administration comprises a priming and at least one booster administration. In certain embodiments thereof, the priming administration is with a HAdV35 comprising nucleic acid encoding a Malaria protein according to the invention and the booster administration is with a HAdV26 comprising nucleic acid encoding said Malaria protein. In other embodiments thereof, the priming administration is with HAdV26 and the booster administration is with HAdV35. In other embodiments, both the priming and booster administration are with HAdV35. In certain embodiments, the priming administration is with HAdV35 and the booster administration is with a Malaria protein. In all these embodiments, it is possible to provide further booster administrations with the same or other vectors or protein.

In certain embodiments, the administration comprises a single administration of a recombinant adenovirus according to the invention, without further (booster) administrations. Such embodiments are advantageous in view of the reduced complexity and costs of a single administration regimen as compared to a prime-boost regimen. Complete protection is already observed after single administration of the recombinant adenoviral vectors of the invention without booster administrations in the cotton rat model in the examples herein.

The invention is further explained in the following examples. The examples do not limit the invention in any way. They merely serve to clarify the invention.

EXAMPLES

Example 1

Generation and Characterization of the pIX-CS$_{short}$ Modified HAdV35 and HAdV26 Vectors Generation of E1 pIX-CS$_{short}$ Modified Vectors With or Without the Malaria *P. Falciparum* CS Protein Transgene (TG)

Replication Deficient Human Adenovirus Vector (HAdVv) Generation

For the generation of replication deficient human Adenovirus 35 (HAdV35) and Human Adenovirus 26 (HAdV26) vectors encoding the CS or CS$_{short}$ transgene and/or pIX-CS or CS$_{short}$, modifications are primarily inserted into the left part of the HAdV genome, namely pAdapt35.Bsu/pShuttle26 plasmids. The rescue of the HAdV35 vectors was subsequently performed by a three plasmid system where the right end of the genome pBr.HAdV35 PRdE3 5E4 orf6/7 (digested with PacI and NotI), and pWE.HAdV35.dpIX.EcoRV, (digested with NotI and EcoRV) and the left end of the genome pAdapt35.Bsu.pIX-mod, (digested with PacI) were transfected into PER.C6® cells using Lipofectamine (Invitrogen) according to the manufacturer's recommendations. The viruses were plaque purified and further propagated on PER.C6® cells supplemented with 10% of fetal bovine serum (FBS) (Life Technologies Inc.) and 10 mM MgCl$_2$, as previously described by Havenga et al. 2006 (6).

The HAdV26 vectors were generated by allowing homologous recombination (HR) between the left (pShuttle26.pIX-mod, digested with PmeI and SbfI) and the right end cosmid (pWE.HAdV26.dE3.5orf6, digested with PacI) in BJ5183 *E. coli* cells as previously described (Chartier et al. 1996). The PacI linearized HAdV26 genome is transfected into PER.C6® cells using Lipofectamine (Invitrogen) according to the manufacturer's recommendations and further amplified in adherent PER.C6® cells at 37° C./10% CO$_2$ in Dulbecco's modified Eagle's medium supplemented with 10% of fetal bovine serum (Life Technologies Inc.) and 10 mM MgCl$_2$.

The replication deficient virus was purified by standard two-step CsCl-gAdient and dialyzed in formulation buffer 10 mM Tris (pH 7.4), 1 mM MgCl2, 75 mM NaCl, 5% sucrose, 0.02% PS-80, 0.1 mM EDTA, 10 mM Histidine, and 0.5% ETOH). The virus concentration viral particles per ml (VP/ml) and infectivity unit per ml (IU/ml) titers were determined by optical density in the presence of SDS (Maizel et al. 1968) and infectivity titrated by $TCID_{50}$ assay. As it can be observed in Table 1 the pIX-modified vectors did not differ from the pIX-native control vectors (Ad.empty) in terms of the VP/ml titers (range $1\times10^{11}$-$5\times10^{12}$) and/or IU/ml titers (range $1\times10^{10}$-$5\times10^{11}$). In addition, the VP/IU (range of 0-30, with three exceptions) ratios and the productivity in PER.C6® cells (VP/cm$^2$, range $5\times10^7$-$5\times10^9$) were determined (Table 1). The VP/ml, IU/ml, VP/IU ratio and the productivity in PER.C6® cells of the pIX-modified vectors is comparable to the control (native pIX) vectors, hence this suggests that the pIX-modification did not have a detrimental effect on the titers and productivity in PER.C6® cells (Table 1).

The "transgene only" vectors: HAdV35.Empty (no transgene), HAdV35.CS$_{short}$ and HAdV35.CS were used as a control for the "pIX modified" vectors with or without the transgene, HAdV35.Empty.pIX-CS$_{short}$, HAdV35.CS.pIX-CS$_{short}$, HAdV35.Empty.pIX-CS and HAdV35.CS.pIX-CS (FIG. 1B).

(VP/well) concentration. The reduced and denatured purified viral particles were separated on pre-cast 12% Bis/Tris Nu-PAGE gel (Invitrogen) in MOPS buffer (Invitrogen) at 175 V, 500 mA. The protein was subsequently transferred to a nitrocellulose membrane according to manufacturer's recommendations using iBlot® Transfer stacks (iBlot system; Invitrogen). The staining was performed for 1 hour with anti-CS specific antibodies (2A10) (or anti-HAdV35.pIX monoclonal) and anti-fiber (HAdV5 4D2, Abcam) as a loading control in 5% Non-fat dry milk (BioAd)/Tris buffered Saline Tween 20 (Invitrogen). Visualization of the protein of interest was achieved by staining with fluorescently labeled IRDye800CW® 1:10 000 goat anti-mouse and recorded on the Odyssey® (Li-Cor).

Figure 1C:
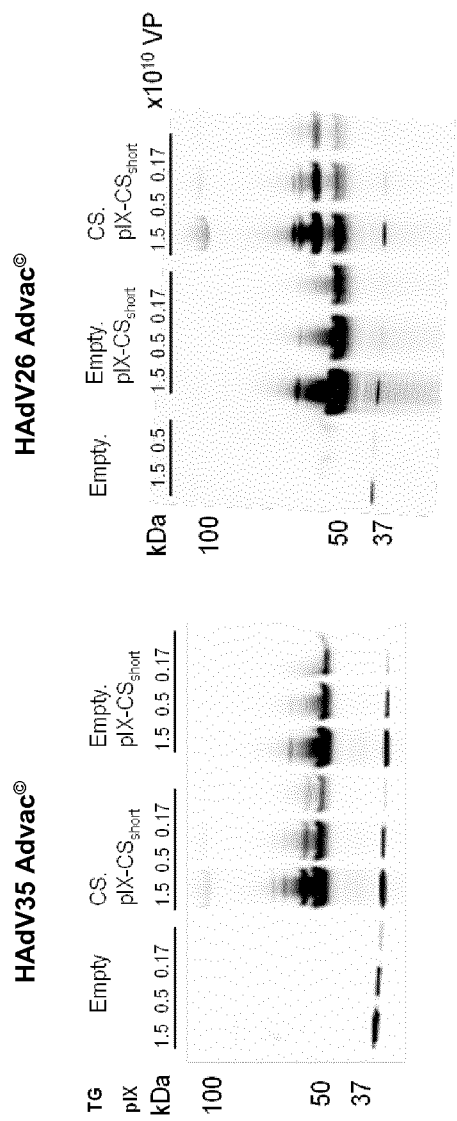

Direct comparison of the pIX-CS$_{short}$ (~32 kDa) in the capsid of HAdV35.Empty.pIX-CS$_{short}$, HAdV35.CS.pIX-CS$_{short}$ and negative control vector HAdV35.Empty, stained with the anti-CS antibody (2A10) and anti-fiber antibody (4D2), shows a comparable content in the pIX-CS$_{short}$ between the CS transgene encoding and Empty vectors at equal loading (fiber protein~35 kDa) per well (FIG. 1C, left WB and Table 2). The same can be observed for the HAdV26.Empty or CS transgene pIX-CS$_{short}$ vectors. There

TABLE 1

Characteristics pIX-modified HAdV26 and HAdV35 vectors

| Vector | TG | pIX | Batch | VP/ml | $TCID_{50}$ | VP/IU ratio | VP/cm2 |
|---|---|---|---|---|---|---|---|
| HAdV26 AdVac © | Empty | NA | | $1.7 \times 10^{12}$ | $1.2 \times 10^{11}$ | 14 | $1.8 \times 10^9$ |
| | Empty | CS$_{short}$ | | $2.0 \times 10^{12}$ | $2.2 \times 10^{10}$ | 94 | $2.9 \times 10^8$ |
| | CS | CS$_{short}$ | | $1.3 \times 10^{12}$ | $2.6 \times 10^{10}$ | 50 | $1.9 \times 10^8$ |
| | Empty | 45-CS$_{short}$ | | $1.9 \times 10^{12}$ | $8.0 \times 10^{10}$ | 23 | $9.5 \times 10^8$ |
| | Empty | SP1-CS$_{short}$ | | $1.5 \times 10^{12}$ | $5.3 \times 10^{10}$ | 34 | $2.3 \times 10^9$ |
| | Empty | SP3-CS$_{short}$ | | $1.1 \times 10^{12}$ | $5.3 \times 10^{10}$ | 21 | $6.8 \times 10^8$ |
| | Empty | SP4-CS$_{short}$ | | $2.1 \times 10^{12}$ | $8.0 \times 10^{10}$ | 27 | $1.7 \times 10^9$ |
| HAdV35 AdVac © | Empty | NA | | $1.0 \times 10^{12}$ | $3.3 \times 10^{11}$ | 3 | $6.1 \times 10^8$ |
| | CS | GlyCS$_{short}$ | | $2.8 \times 10^{12}$ | $2.0 \times 10^{11}$ | 13 | NA |
| | Empty | GlyCS$_{short}$ | | $3.3 \times 10^{12}$ | $2.9 \times 10^{11}$ | 11 | NA |
| | Luc | GlyCS$_{short}$ | | $4.8 \times 10^{11}$ | $4.9 \times 10^{10}$ | 10 | NA |
| | Empty | CS$_{short}$ | | $2.6 \times 10^{12}$ | $4.2 \times 10^{11}$ | 6 | NA |
| | CS | CS$_{short}$ | | $1.5 \times 10^{12}$ | $2.0 \times 10^{11}$ | 8 | $8.8 \times 10^8$ |
| | Empty | 45-CS$_{short}$ | | $1.4 \times 10^{12}$ | $1.8 \times 10^{11}$ | 8 | $2.5 \times 10^8$ |
| | CS | 45-CS$_{short}$ | 1 | $2.8 \times 10^{11}$ | $1.7 \times 10^{10}$ | 17 | $1.3 \times 10^6$ |
| | CS | 45-CS$_{short}$ | 2 | $5.9 \times 10^{11}$ | $1.5 \times 10^{11}$ | 4 | $2.9 \times 10^8$ |
| | Empty | Gly45-CS$_{short}$ | | $1.1 \times 10^{12}$ | $6.0 \times 10^{10}$ | 19 | $6.3 \times 10^8$ |
| | CS | Gly45-CS$_{short}$ | | $1.9 \times 10^{12}$ | $1.8 \times 10^{11}$ | 11 | $1.8 \times 10^9$ |
| | Empty | CSfull* | 1 | $2.5 \times 10^{11}$ | $3.7 \times 10^{10}$ | 7 | $5.9 \times 10^7$ |
| | Empty | CSfull* | 2 | $1.8 \times 10^{12}$ | $1.4 \times 10^{11}$ | 13 | $1.7 \times 10^8$ |
| | CS | CSfull* | 1 | $4.5 \times 10^{11}$ | $3.6 \times 10^{11}$ | 12 | NA |
| | CS | CSfull* | 2 | $6.8 \times 10^{11}$ | $5.6 \times 10^{10}$ | 12 | $3.0 \times 10^8$ |
| | Empty | SP1-CS$_{short}$ | | $2.2 \times 10^{12}$ | $3.3 \times 10^{11}$ | 7 | $3.8 \times 10^9$ |
| | Empty | SP2-CS$_{short}$ | | $3.4 \times 10^{12}$ | $2.2 \times 10^{11}$ | 15 | $1.1 \times 10^9$ |
| | Empty | SP3-CS$_{short}$ | | $3.3 \times 10^{12}$ | $4.9 \times 10^{11}$ | 7 | $7.5 \times 10^9$ |
| | Empty | SP4-CS$_{short}$ | | $2.4 \times 10^{12}$ | $3.3 \times 10^{11}$ | 7 | $4.1 \times 10^9$ |
| | Empty | mHA(ecto)* | | $1.6 \times 10^{12}$ | $4.0 \times 10^{11}$ | 4 | NA |
| | mHA | mHA(ecto)* | | $1.8 \times 10^{12}$ | $2.7 \times 10^{11}$ | 7 | NA |
| | Empty | mHA.GCN(ecto)* | | $1.6 \times 10^{12}$ | $4.9 \times 10^{11}$ | 3 | NA |
| | mHA.GCN | mHA.GCN(ecto)* | | $1.7 \times 10^{12}$ | $4.9 \times 10^{11}$ | 8 | NA |
| | Empty | HA(ecto)* | | $1.9 \times 10^{12}$ | $1.2 \times 10^{11}$ | 16 | NA |
| | HA | HA(ecto)* | | $1.4 \times 10^{12}$ | $1.8 \times 10^{11}$ | 8 | NA |

*pIX not incorporated into the capsid, NA: not available pIX-CS and pIX-CS$_{short}$ Capsid Incorporation and Transgene Expression Assessment by Western Blot Capsid incorporation of pIX-CS and/or pIX-CS$_{short}$ variants was performed by Western Blot (WB) of purified viral particles at 1.5, 0.5 and $0.17 \times 10^{10}$ viral particles per well is no apparent difference between the capsid incorporated pIX-CS$_{short}$ in either HAdV26 with or without (empty) encoded CS transgene at equal loading (fiber protein ~40 kDa visible at the highest concentration VP/well) (FIG. 1C, right WB and Table 3).

TABLE 2

Capsid incorporation pIX-modifications

| Capsid modification | | pIX fusion a.a. | Capsid incorporation (n) |
|---|---|---|---|
| TG | pIX | | |
| HAdV35 CS | CSshort | 151 | ++++ (3) |
| Advac© Luc | CSshort | 151 | ++++ (3) |
| Empty | CSshort | 151 | ++++ (3) |
| CS | Gly-CSshort | 154 | ++++ (2) |
| Empty | Gly-CSshort | 154 | ++++ (2) |
| CS | 45-CSshort | 185 | ++++ (2) |
| Empty | 45-CSshort | 185 | ++++ (2) |
| CS | Gly45-CSshort | 188 | ++++ (2) |
| Empty | Gly45-CSshort | 188 | ++++ (2) |
| Empty | SP1-CSshort | 183 | ++++ (1) |
| Empty | SP2-CSshort | 184 | +++ (1) |
| Empty | SP3-CSshort | 181 | ++ (1) |
| Empty | SP4-CSshort | 183 | + (1) |
| CS | CSFULL | 376 | – (2) |
| Empty | CSFULL | 376 | – (2) |
| mHA | mHA(ecto) | 248 | – (2) |
| Empty | mHA(ecto) | 248 | – (2) |
| mHA.GCN | mHA.GCN(ecto) | 305 | – (2) |
| Empty | mHA.GCN(ecto) | 305 | – (2) |
| HA | HA(ecto) | 512 | – (2) |
| Empty | HA(ecto) | 512 | – (2) |

++++: very good,
+++: good,
++: poor,
+: barely detected and
–: not detected
(n) = number of experiments,
a.a.: amino acids

TABLE 3

Capsid incorporation pIX-modifications

| Capsid modification | | pIX fusion a.a. | Capsid incorporation (n) |
|---|---|---|---|
| TG | pIX | | |
| rHAdV26 Empty | $CS_{short}$ | 151 | ++++ (2) |
| Advac© CS | $CS_{short}$ | 151 | ++++ (2) |
| Luc | $CS_{short}$ | 151 | ++++ (2) |
| Empty | SP1-$CS_{short}$ | 183 | ++++ (1) |
| Empty | SP3-$CS_{short}$ | 181 | ++++ (1) |
| Empty | SP4-$CS_{short}$ | 183 | ++++ (1) |
| Empty | 45-$CS_{short}$ | 185 | ++++ (1) |

++++: very good,
+++: good,
++: poor,
+: barely detected and
–: not detected
(n) = number of experiments,
a.a.: amino acids In addition to the capsid pIX-$CS_{short}$ (~32 kDa) in the CS transgene encoding vectors, the CS protein (~42 kDa) itself is also detected in the purified HAdV26 and HAdV35 batches, which suggests nonspecific association to the capsid or at least co-purification (FIG. 1C). Assessment of capsid incorporation of pIX-CS in the HAdV35 pIX-CS modified vectors with and without CS as a transgene, by staining purified vectors with anti-CS (2A10) showed no capsid incorporation of the pIX-CS (Table 2). To ensure that the lack of capsid incorporation of pIX-CS in the HAdV35.Empty.pIX-CS and HAdV35.CS.pIX-CS was not due to decreased or absent expression of the pIX-CS modification in the PER.C6® cells during production of the vector, PER.C6® cell lysates infected with 5000 VP/cell were tested on WB and stained with anti-HAdV35.pIX monoclonal antibody. The WB analysis shows expression of pIX-CS (~55 kDa) in PER.C6® infected with either the HAdV35.CS and Empty pIX-CS modified vectors (data not shown). The latter suggest that the lack of pIX-CS in the capsid is due to the inefficient incorporation of the CS protein fused to pIX into the viral capsid and not the lack of pIX-CS protein expression during the production of the vector in PER.C6®. It can be concluded that pIX-$CS_{short}$ is efficiently incorporated in both the HAdV26 and HAdV35 viral capsids and that the encoded CS transgene in HAdV26 and HAdV35 vectors had no effect on the incorporation efficiency of pIX-$CS_{short}$. In contrast the pIX-CS was not incorporated into the viral capsid which indicates that the size of the antigen ($CS_{short}$ 151 a.a. vs. CS 376 a.a.) or possibly the tertiary structure might have an effect on the capsid incorporation.

Transgene Expression

Figure 2B:
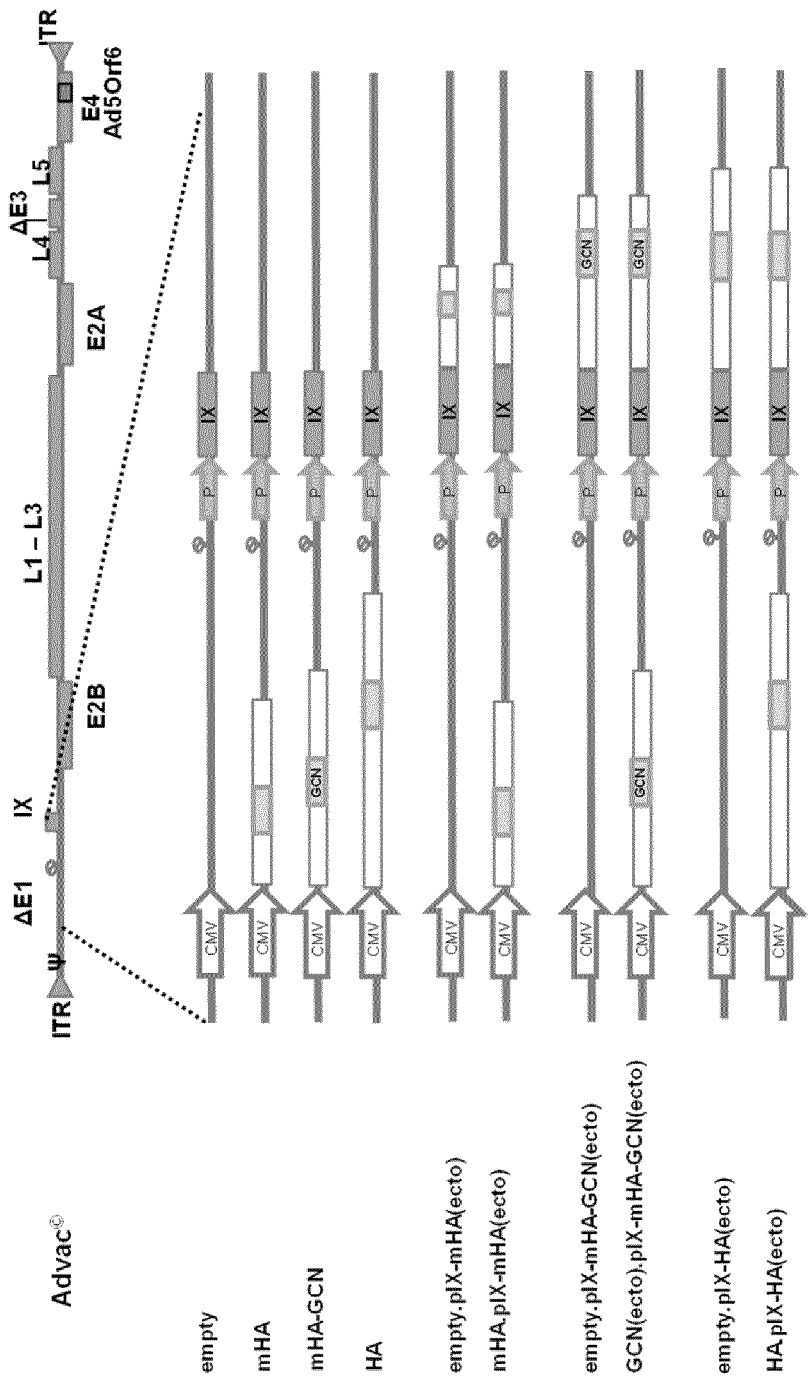
FIG. 2: Direct fusion of Influenza A Hemagglutinin (HA) antigen to pIX (A) Schematic representation of different Influenza A HA antigen designs depicting the HA (512 amino acids (a.a.)) molecule with the corresponding N- & C-termini, signal peptide, membrane domain and the ectodomain (in grey). The middle bar shows the mHA (303 a.a.) protein consisting of the N- & C-termini portions of the HA protein and the ectodomain. The mHA-GCN(ecto) molecule (248 a.a.) lacks the N-terminus signal peptide and the ectodomain of the native HA is replaced with the GCN trimerization domain. (B) Diagram of the HAdV vectors encoding the different HA designs in the E1 region and/or fused to the pIX capsid protein and all the combinations thereof.

In order to ensure that pIX-modified vectors can still express a transgene, we assessed whether pIX-capsid modification could have a possible effect on the transgene expression. The pIX-modified and E1 transgene encoding vectors were tested in A549 cells for the expression of the transgenes under non replicating conditions. A549 cells were transduced with HAdV26.CS.pIX-$CS_{short}$ and HAdV26.Empty.pIX-$CS_{short}$ at 10000, 25000 and 50000 VP/cell or HAdV35.CS.pIX-$CS_{short}$/pIX-CS and HAdV35.Empty.pIX-$CS_{short}$/pIX-CS at 1000, 2500 and 5000 VP/cell, incubated for 48 hours at 37° C., harvested, lysed and analyzed in WB with anti-CS (2A10) antibody. The expression of CS transgene (~42 kDa) of all the pIX-$CS_{short}$ vectors encoding the CS transgene was comparable to the transgene only controls (i.e. HAdV26.CS and HAdV35.CS). In the Firefly luciferase (luc) encoding vectors the expression of luciferase was also determined (data not shown). Due to the endogenous pIX promoter and the possible enhancing effect of the upstream CMV promoter in E1-cassette (Nakai et al 2007) the expression of the pIX-modification is expected and confirmed under non-replicating conditions. Surprisingly however, $CS_{short}$ protein as a transgene (HAdV35.$CS_{short}$) was not detected in A549 cells, indicating some disregulation in protein turnover. Cumulatively these observations imply that (1) fusion of $CS_{short}$ to pIX most probably stabilizes the $CS_{short}$ protein since on its own no viable protein is detected and (2) pIX-$CS_{short}$ modifications do not have an effect on the CS transgene expression in A549 cells. Taken together the $CS_{short}$ fused to pIX did incorporate into the viral capsid and doing so did not impair the transgene expression.

pIX-HA Modified Vectors: Capsid Incorporation and Transgene Expression Assessment by Western Blot As part of the development of an Influenza AdVac© based vaccine, pIX modified vectors were designed displaying different variants of an Influenza A protein in combination with homologous transgenes of these variants in E1. Three different variants of the Influenza A Hemagglutitin (HA) were designed and fused to pIX, namely 512 amino acid HA, 303 amino acids mHA, and 248 amino acids mHA.GCN (ecto) (ect-domain swapped with the GCN domain) with or without the respective proteins integrated as transgene in the E1 region of the same vector (FIG. 2). Analysis of capsid incorporation of the pIX-HA-variants by direct staining of the HAdv35.HA.pIX-HA, HAdV35.Empty.pIX-HA, HAdV35.mHA.pIX-mHA, HAdV35.Empty.pIX-mHA, HAdV35.mHA.GCN.pIX-mHA.GCN(ecto) and HAdV35.Empty.pIX-mHA.GCN(ecto) viral particles (VP) in Western Blot with both polyclonal anti-HA and monoclonal anti-pIX antibodies showed no pIX modified proteins in the capsid (Table 2). However, the transgene expression in A549 cells was confirmed by staining A549 cell lysates transduced with the indicated vectors at 1000, 2500 and 5000 VP/cell (data not shown). The observations were identical for the CS (376 amino acids) fusion to the pIX which, as discussed, did not incorporate into the capsid but was produced during the replication and vector production in PER.C6® cells (data not shown). Overall, efficient capsid incorporation of the $CS_{short}$ (151 a.a.) was observed while no capsid incorporation was observed for the CS (376 a.a.) and the HA variants (248, 303, and 512 a.a.) directly fused to pIX. This indicates that it is difficult to predict which antigens will be efficiently incorporated into the capsid and which antigens will not. An overview of the capsid incorporation efficiency of all the pIX-modified vectors, based solely on the qualitative observations (of band intensities) made in WB analysis by direct comparison to the control vectors is provided in Table 2 and 3.

Immunogenicity of pIX-$CS_{short}$ Capsid Modified Vectors Directly Compared to the Immunogenicity of the CS Protein Determination of CS-Specific Humoral Immune Responses by Antibody-ELISA

*P. falciparum* CS-protein-specific total IgG, or subclass-specific IgG1 and IgG2a responses in serum were determined by an enzyme-linked immunosorbent assay (ELISA) as previously described in (10). Maxisorp™ flat-bottomed 96-well plates (Nunc-Immuno, location) were coated over night at 4° C. with 2 μg/ml of CS-specific (NANP)6C peptide (Pepscan Presto, Netherlands) in 0.05 M carbonate buffer (pH 9.6). Plates were washed in PBS/0.2% Tween20 (PBS-T) and blocked with 1% BSA in PBS/0.02% Tween20 for 1 hour at room temperature, then washed again. Mouse serum samples were diluted in sample buffer (PBS/0.02% Tween/0.2% FBS) at a starting concentration of 1:100, plated in a 2-fold dilution series and incubated at for 2 hours at RT. Plates were washed with PBS-T. Total bound IgG was detected with biotinylated goat-anti-mouse IgG (Dako, location) and streptavidin-conjugated horseAdish peroxidase (HRP; Becton Dickinson). For the detection of IgG subclasses, duplicate plates were incubated in parallel and bound IgG1 or IgG2a was detected with goat-anti-mouse IgG1 or anti IgG2a antibodies directly conjugated to HRP (Southern Biotechnology Associates, Birmingham, Ala.). After washing of the plates with PBS-T, o-Phenylenediamine (OPD; Pierce) was added, the plates developed for 10 minutes and the reaction stopped with 1M $H_2SO_4$ before optical density was determined at 492 nm. Relative serum titers of total IgG (ELISA units/ml) were calculated in comparison to a *P. falciparum* CS-specific reference serum, using a 4-parameter curve fit model. The IgG1- and IgG2a specific measurements were used directly to calculate the ratio between IgG2a and IgG1, by dividing the reciprocal dilution at which the $OD_{492}$ reached three times that of the background measurement in a nave control sample.

Statistical Analysis

The response variables, i.e. EU (ELISA Unit) and SFU (Spot Forming Unit) were log-transformed and group comparisons were performed using ANOVA models. In case of repeated measurements over time, a random intercept was added to the ANOVA model to properly account for correlated observations. Comparisons between groups containing values below the lower limit of quantification were analyzed using censored regression models. A correction for multiple testing was applied using the Dunnett method, since there was a fixed reference group in each analysis. Differences with a $p \leq 0.05$ were considered significant. All statistical analyses were performed using SAS® software, version 9.2 (SAS Institute Inc., 2011).

Figure 1D:
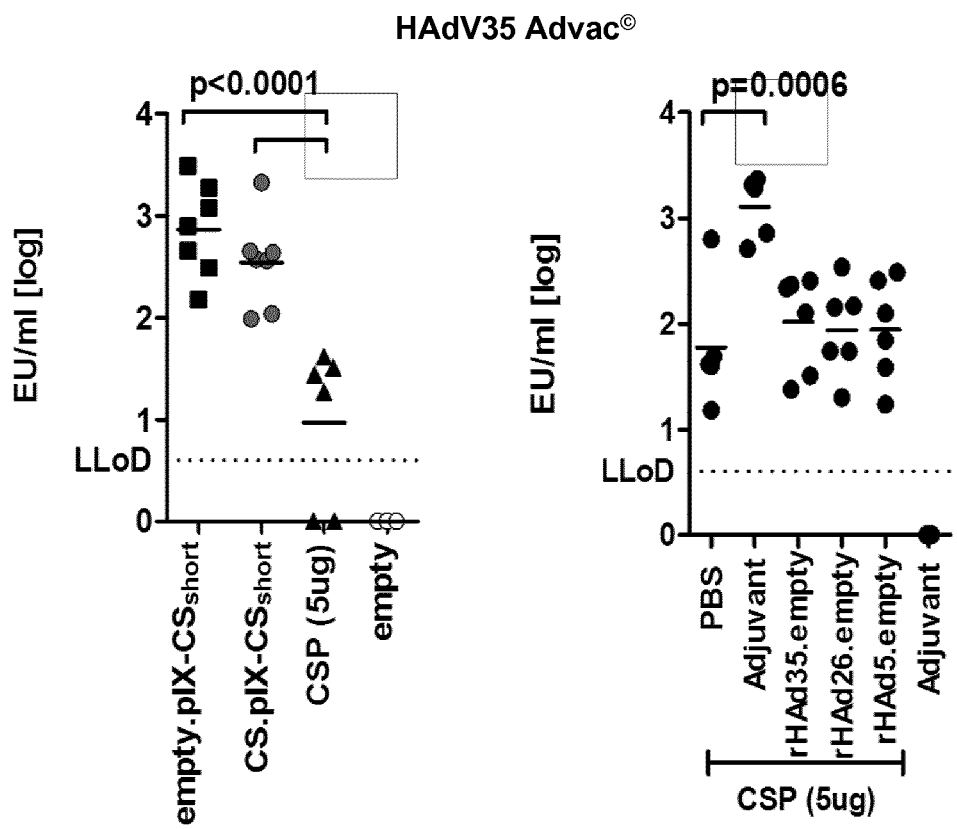

The CS-specific humoral response (B-cell responses) induced by HAdV35.Empty.pIX-$CS_{short}$ and HAdV35.CS.pIX-$CS_{short}$ was tested in mice and compared to CS protein (CSP). Balb/C mice (n=7 per group) were immunized intramuscularly with $1 \times 10^{10}$ VP HAdV35.Empty.pIX-$CS_{short}$, HAdV35.CS.pIX-$CS_{short}$ or 5 μg (unadjuvanted) yeast-produced CSP. Mice immunized with $1 \times 10^{10}$ VP HAdV35.empty vector served as a negative control. CS-specific B-cell responses were determined at week 4 post immunization. Both pIX-$CS_{short}$ vectors induced high CS-specific total IgG titers that highly exceeded those induced by the CSP ($p \leq 0.0001$ ANOVA with Dunnett correction for multiple comparisons), indicating that the display of the CS antigen on the capsid of the viral particles is a very potent platform, even compared to the highly immunogenic CS protein (FIG. 1D left panel). To determine whether the relatively high immunogenicity of the pIX-$CS_{short}$ vectors is mediated by a potentially adjuvating effect of the vector itself, Balb/C mice were immunized intramuscularly with 5 μg CSP alone or mixed with $1 \times 10^{10}$ VP HAdV35.empty, HAdV26.empty or HAdV5.empty (n=6 mice per group). 5 μg adjuvanted CSP was taken as a reference point and adjuvant only served as a negative control.

4 weeks after immunization CS-specific IgG titers in mice immunized with adjuvanted CSP exceeded those induced with CSP protein alone (p=0.0006, ANOVA with Dunnett correction for multiple comparisons) and reached levels similar to those observed in animals immunized with $1 \times 10^{10}$ VP of pIX-$CS_{short}$ modified HAdV35 vectors at the same time point post immunization. No statistically significant (p=0.8) increase in CS-specific IgG titers was observed in the mice immunized with HAdV.empty vectors mixed with CSP when compared to the CSP protein alone (FIG. 1D). Balb/C mice immunized with a dose range of $1 \times 10^7$, $1 \times 10^8$, $1 \times 10^9$, or $1 \times 10^{10}$ VP HAdV35.Empty.pIX-$CS_{short}$ compared to the HAdV35.CS transgene only vector, were more potent over a period of 8 weeks post immunization at inducing CS-specific IgG titers (data not shown). The immunogenicity of the HAdV26.Empty.pIX-$CS_{short}$ and HAdV26.CS.pIX-$CS_{short}$ compared to the HAdV26.CS transgene only vector was also determined in mice. Balb/C mice were immunized with a dose range of $1 \times 10^7$, $1 \times 10^8$, $1 \times 10^9$, or $1 \times 10^{10}$ VP HAdV26.Empty.pIX-$CS_{short}$, HAdV26.CS.pIX-$CS_{short}$ and HAdV26.CS. As a negative control HAdV26.empty was used at the highest dose $1 \times 10^{10}$ VP per animal (n=5). The results observed were similar to those with the HAdV35 pIX-$CS_{short}$; in overall, 4 weeks post immunization, the pIX-modified vectors were more potent at inducing CS-specific IgG titers at all doses, than the CS transgene only vector (data not shown). In sum, pIX-$CS_{short}$ modified vectors are more potent than a CS protein alone or a HAdV35.CS transgene vector (without the pIX-$CS_{short}$ fusion protein) at inducing CS-specific antibody responses. This effect cannot be achieved by mixing the protein with the HAdV.Empty vectors suggesting that the fusion of the $CS_{short}$ protein to the capsid is necessary for induction of superior antigen specific antibody responses.

Example 2

Generation and Characterization of pIX-$CS_{short}$ Modified HAdV35 and HAdV26 Vectors Containing a Spacer Between the pIX and the $CS_{short}$ HAdV35 and HAdV26 vectors were modified by fusing a $CS_{short}$ protein to pIX via a 45 Å spacer (16, Vellinga et al.

Figure 3A:
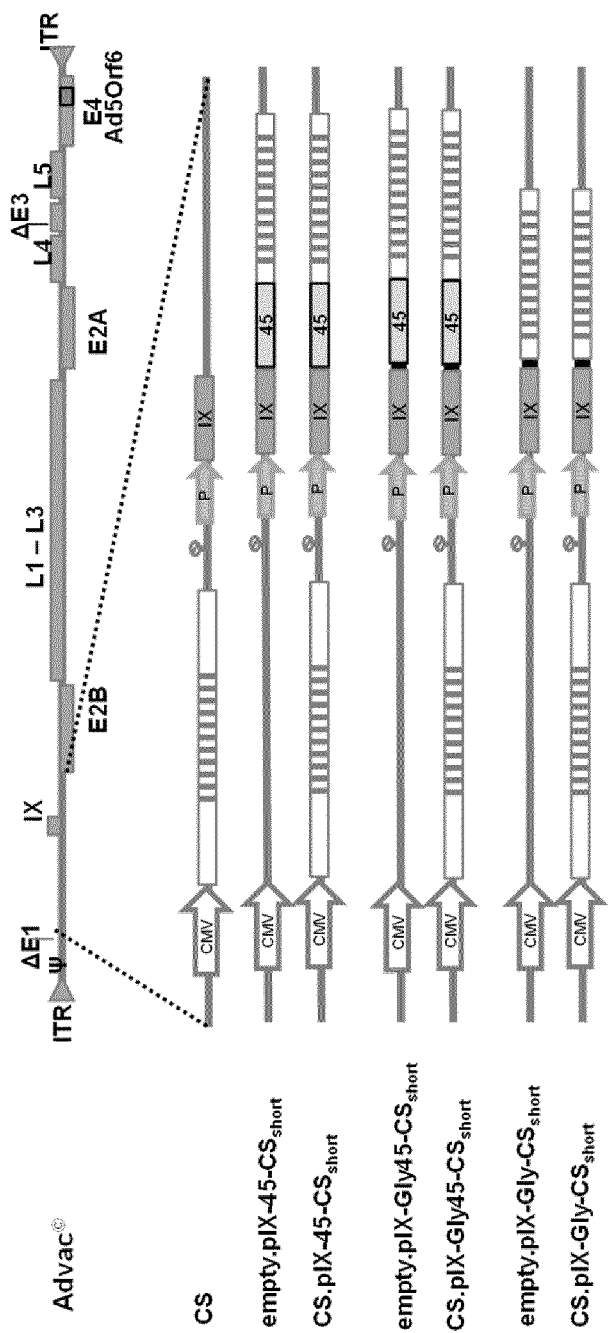
FIG. 3: $CS_{short}$ antigen fusion to HAdV pIX via an alpha-helix spacer (A) The schematically depicted HAdV vectors designed with $CS_{short}$ fused to the pIX via 45 Å alpha-helix spacer (16), Gly-linker and Gly-45 Å. The pIX modified vectors are made both with and without the CS transgene in the E1-cassette. (B) To compare the incorporation efficiency of the vectors with and without the CS transgene and the different pIX-$CS_{short}$ modifications in the capsid, Western Blots are shown with a serial dilution of 1.5, 0.5 and $0.17\times10^{10}$ VP/per well of the HAdV35.Empty/ CS.pIX-45 Å-pIX-$CS_{short}$, HAdV35.Empty/CS.pIX-Gly45 Å-pIX-$CS_{short}$ and HAdV35.Empty/CS.pIX-GlypIX-$CS_{short}$ stained with anti-CS specific (2A10) antibody and anti-fiber (4D2) as a loading control. As a non-modified pIX control a HAdV35.empty vector is taken along. Expected size of the CS transgene is ~42 kDa and pIX-$CS_{short}$ protein variants ~35 kDa, however both proteins migrate higher in the gel due to the NANP-repeat. (C) The CS-specific antibody (EU/ml log) responses 8 weeks post immunization with 1×10⁸, 1×10⁹, or 1×10¹⁰ VP/animal of HAdV35.empty.pIX-45-CS$_{short}$, HAdV35.CS.pIX-45-CS$_{short}$, a mix of HAdV35.empty.pIX-45-CS$_{short}$ and HAdV35.CS, HAdV35.CS alone, or HAdV35.empty (10⁹ VP/animal only) in mice are depicted in the graphs. (D) The two graphs show the IFNγ ELISPOT responses post immunization against the entire P. falciparum CS protein sequence or the H-2Kd restricted immunodominant HAdV35 hexon epitope KYTPSNVTL. Statistical significance was determined using a two-way ANOVA test with Dunnett correction for multiple comparisons on log-transformed data by time point and dose. Black horizontal bars p≤0.05.
Figure 3B:
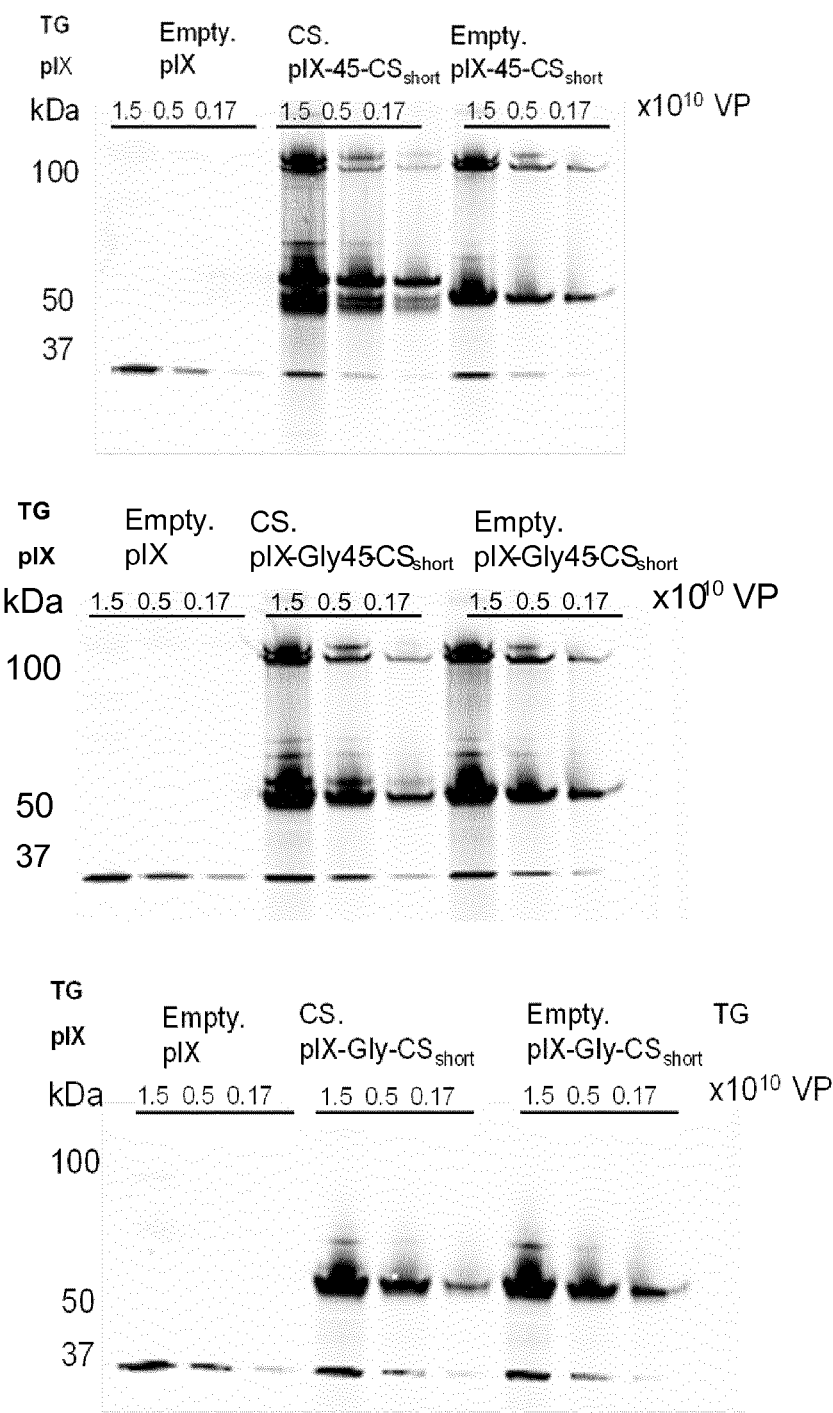

2004) only, a 45 Å spacer combined with a Gly-linker for added flexibility or a Gly-linker only. The sequence of the 45 Å spacer can be found in Table 4. HAdV35.pIX-45-CS$_{short}$, HAdV35.pIX-Gly45-CS$_{short}$ and HAdV35.pIX-Gly-CS$_{short}$ vectors with or without CS transgene in E1 were generated in PER.C6® as indicated above for the HAdV35 direct fusion (pIX-CS$_{short}$) vectors (FIG. 3A and Table 1).

pIX-CS$_{short}$ Spacer Variants Capsid Incorporation and Transgene Expression Assessment by Western Blot Capsid incorporation of pIX-CS$_{short}$ spacer variants was assessed by WB as described above. Purified viral particles 1.5, 0.5 and 0.17×10$^{10}$ VP/well were reduced, denatured, separated on gel and transferred to a nitrocellulose membrane. The staining of pIX-CS$_{short}$ spacer variants was performed with a CS-specific antibody (2A10) and anti-fiber antibody (4D2) as a loading control, where the HAdV35.empty vector served as a negative control. To ensure that the CS transgene has no effect on the capsid incorporation of the different spacer variant pIX-CS$_{short}$ modifications all the vectors with and without the transgene were compared side by side. At comparable loading (fiber band ~35 kDa), the WB results show no difference in capsid incorporation of pIX-CS$_{short}$ spacer variant, between the vectors encoding the CS transgene in E1 and the empty vectors. The same as with the pIX-CS$_{short}$ direct fusion modifications, in purified vectors encoding the CS transgene, the CS transgene seems to be co-purified with the pIX spacer vectors. An obvious difference between the 45-spacer containing vectors and either the Gly-only or direct fusion CS$_{short}$ is a band migrating at approximately 100 kDa in addition to the pIX-fusion protein (FIG. 3B). This might be an assay artefact or an unknown effect of the 45-spacer on the pIX and CS$_{short}$ modification. Direct head to head comparison of the different pIX-CS$_{short}$ variants, including the direct fusion, stained with anti-CS antibody (2A10) shows comparable levels of pIX incorporated in the capsid between all the vectors. It seems that the addition of the spacer or the Gly-linker does not have a detrimental effect on the capsid incorporation efficiency. pIX-45-CS$_{short}$, PIX-Gly45-CS$_{short}$ and pIX-Gly-CS$_{short}$ are efficiently incorporated into the viral capsid in vectors with and without the CS transgene.

Spacer pIX-CS$_{short}$ Capsid Modified Vectors Immunogenicity Directly Compared to the CS Transgene Vector The CS-specific B-cell responses against the HAdV35.empty.pIX-Gly45-CS$_{short}$, HAdV35.CS.pIX-Gly45-CS$_{short}$, HAdV35.empty.pIX-Gly-CS$_{short}$, HAdV35.CS.pIX-Gly-CS$_{short}$, HAdV35.CS.pIX-45-CS$_{short}$, HAdV35.empty.pIX-45-CS$_{short}$ vectors were determined in mice and directly compared to the HAdV35.CS control vector. Balb/C mice (n=5) were immunized intramuscularly at a dose range of 1×10$^7$, 1×10$^8$, 1×10$^9$, 1×10$^{10}$ VP. Animals immunized with 1×10$^{10}$ VP of HAdV35.empty served as a negative control. Total CS-specific IgG responses in the serum were measured at 2-week intervals over a period of 8 weeks post immunization. At 1×10$^7$ VP/mouse, none of the tested vectors mounted immune responses above the lower assay limit of quantification. At 1×10$^8$ all constructs displaying the CS$_{short}$ induced CS-specific IgG responses by week 4 post immunization and these responses were maintained until the end of the experiment at week 8. HAdV35.CS showed comparatively lower potency, with the lowest dose to induce CS-specific IgG responses being 1×10$^9$ VP. Across all doses that induced detectable CS-specific responses, overall titers elicited by the four vectors pIX-CS$_{short}$ via pIX were higher than those induced by HAdV35.CS. CS$_{short}$ display on any of the three spacer constructs proved to further increase immunogenicity, resulting both in earlier induction of CS-specific IgG responses compared to the pIX-CS$_{short}$ modified vector and titers that were significantly higher than those induced by HAdV35.CS (1×10$^8$-1×10$^{10}$ VP; mixed models analysis). Although the three different spacer constructs induced CS-specific IgG titers of comparable magnitude, HAdV35.empty.pIX-45-CS$_{short}$ proved to be the only vector consistently reaching responses that significantly exceeded HAdV35.CS at all three immunogenic doses (1×10$^8$-1×10$^{10}$ VP) (data not shown).

Immune Responses Against the CS Transgene in pIX-45-CS$_{short}$ Capsid Modified Vectors The induction of cellular immune responses in addition to humoral responses against the Malaria causing agent P. falciparum, is considered a desirable feature of a protective vaccine against infection at the pre-erythrocytic stage. Adenoviral vectors are characterized by strong induction of T cell responses against encoded transgenes, as evidenced by high CD4+ and CD8+ T cell responses detected in mice and nonhuman primates immunized with HAdV35.CS (Radosevic et al. 2011, Rodriguez et al. 2009). We therefore assessed whether implementation of pIX-display of the B-cell epitope carrying CS$_{short}$ antigen on HAdV35 encoding the CS transgene (including the immune-dominant H-2KD restricted CD8+ T cell epitope NYDNAGTNL) would maintain the induction of strong humoral immune responses as seen before, and whether this combination would impact T cell responses against the encoded transgenes.

For this purpose, the CS-specific humoral responses induced by the HAdV35.empty.pIX-45-CS$_{short}$ and HAdV35.CS.pIX-45-CS$_{short}$ were tested in Balb/C mice (n=5) immunized intramuscularly with a dose titration 1×10$^8$, 1×10$^9$ and 1×10$^{10}$ VP/animal. The vectors were directly compared to the HAdV35.empty.pIX-45-CS$_{short}$ HAdV35.CS transgene vector mix, HAdV35.CS alone and HAdV35 was used as a negative control. To adjust the VP number given to the group receiving the mix (HAdV35.empty.pIX-45-CS$_{short+}$ HAdV35.CS), the total VP number in the remaining groups was supplemented by using HAdV35.empty, which resulted in a formal total vector dose of 2×10$^8$-2×10$^{10}$ VP/mouse.

Figure 3C:
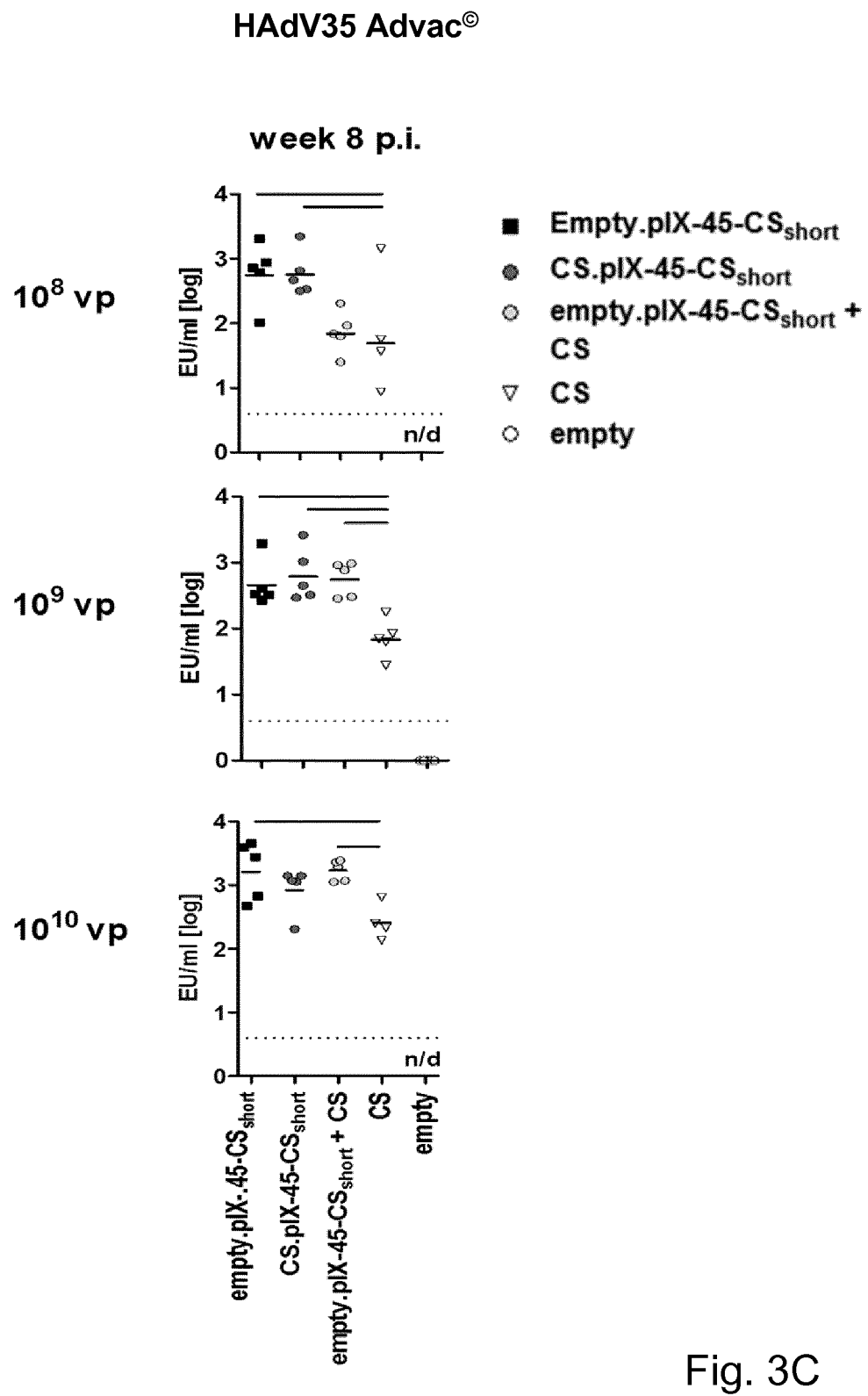

CS-specific total IgG responses in serum were measured at 8 weeks post immunization (FIG. 3C). In contrast to HAdV35.CS and similarly to HAdV35.empty pIX-45-CS$_{short}$, HAdV35.CS.pIX-45-CS$_{short}$ induced measurable CS-specific antibody responses at the lowest dose (1×10$^8$), indicating higher potency of the vector compared to pIX-unmodified HAdV35.CS. In addition, the titers mounted by both HAdV35.CS.pIX-45-CS$_{short}$ and HAdV35.empty pIX-45-CS$_{short}$ at week 2 at 1×10$^{10}$ VP strongly exceeded those induced by HAdV35.CS at the same dose of 1×10$^{10}$ VP (p≤0.005 for all comparisons, FIG. 3C). Although the overall titers in all groups increased in magnitude over time, those induced by HAdV35.CS remained significantly lower than those induced by the two pIX-45-CS$_{short}$ fusion constructs at week 8 post immunization (p≤0.005 for all comparisons in the groups receiving 1×10$^8$ and 1×10$^9$ VP, FIG. 3C). Application of the HAdV35.empty.pIX-45-CS$_{short}$ fusion construct and HAdV35.CS in the equal mix also resulted in significantly increased CS-specific titers at all doses and time points, with the exception of the lowest dose, 1×10$^8$, where the difference in titers did not reach significance at week 8 post immunization. This indicates that immune responses against the transgene do not interfere with the induction of humoral responses against the pIX-$CS_{short}$ fusion construct.

Figure 3D:
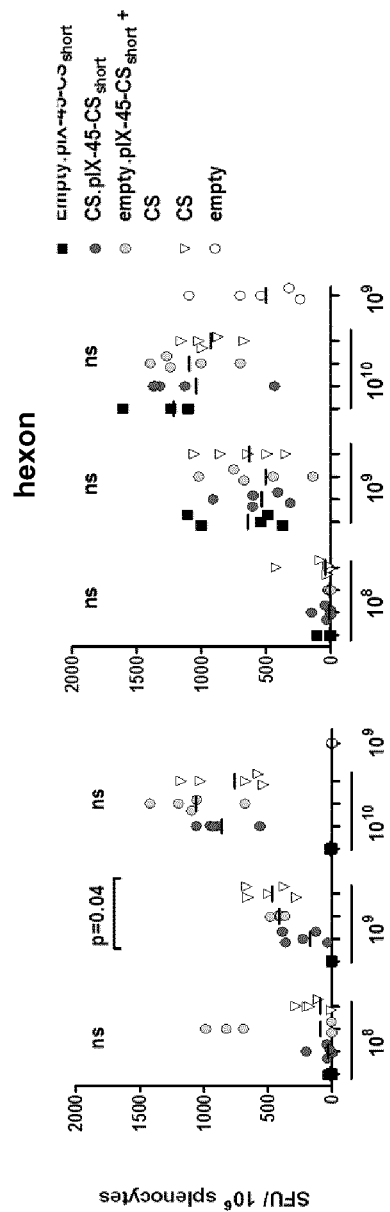

Determination of CS- and HAdV35 Hexon-Specific Cellular Immune Responses by ELISPOT Antigen-specific cellular immune responses in vaccinated mice were assessed using an IFNγ enzyme-linked immune-spot assay (ELISPOT) based on the method previously described in (10). Freshly isolated splenocytes were incubated either with a pool of 15-mer peptides overlapping by 11 amino acids, spanning the entire sequence of the *P. falciparum* CS protein, with the described H-2Kd-MHC class I-restricted, immunodominant NYDNAGTNL CS epitope, or with the immunodominant HAdV35 hexon epitope KYTPSNVTL restricted by the same MHC class I epitope. The peptide pools and single peptides were used at a final concentration of 1 ug/ml for each individual peptide. 96-well multiscreen plates (Millipore, Bedford, Mass.) were coated overnight with 100 μl/well of 10 μg/ml anti-mouse IFN-γ (BD Pharmingen, San Diego, Calif.) in endotoxin-free Dulbecco's phosphate-buffered saline (D-PBS). The plates were then washed three times with D-PBS containing 0.05% Tween 20 (D-PBSTween), blocked for 2 h with D-PBS containing 5% fetal bovine serum (FBS) at 37° C., and rinsed with RPMI 1640 containing 10% FBS. Splenocytes from individual mice were stimulated with the CS peptide pool, the CS 9-mer or the HAdV35 hexon 9-mer for 18 h at 37° C. Following incubation, the plates were washed six times with D-PBSTween and once with distilled water. The plates were then incubated with 2 μg/ml biotinylated anti-mouse IFN-γ (BD Pharmingen, San Diego, Calif.) for 2 h at room temperature, washed six times with D-PBSTween, and incubated for 2 h with a 1:500 dilution of streptavidin-alkaline phosphatase (Southern Biotechnology Associates, Birmingham, Ala.). Following six washes with D-PBSTween and one with PBS, the plates were developed with nitroblue tetrazolium-5-bromo-4-chloro-3-indolyl-phosphate chromogen (Pierce, Rockford, Ill.), the reaction was stopped with tap water, the plates air dried, and read using an ELISPOT reader (Aelvis GmbH). The numbers of spot-forming units (SFU) per $10^6$ cells were calculated. CS-specific cellular immune responses were assessed against all four constructs by ELISPOT (peptides spanning the entire CS protein sequence) at week 8 post prime (FIG. 3D). Due to the absence of the immune-dominant T cell epitope NYDNAGTNL in the $CS_{short}$ sequence, HAdV35.empty.pIX-45-$CS_{short}$ did not induce any cellular immune responses, as expected. All other immunization regimen induced responses followed a dose-titration relationship, with increasing responses corresponding to increasing doses. IFNγ responses induced by HAdV35.CS.pIX-45-$CS_{short}$ did not significantly differ from those induced by HAdV35.CS at $1\times10^8$ and $1\times10^{16}$ VP dose, but were slightly reduced at the intermediate dose of $1\times10^9$ VP (p=0.04). Responses induced by the equal mix of HAdV35.empty.pIX-45-$CS_{short}$ and HAdV35.CS did not differ from those induced by HAdV35.CS at any of the given doses. As vaccination control, IFNγ responses targeting the immune-dominant H-2Kd restricted epitope KYTPSNVTL in HAdV35 hexon were measured, which, as expected, did not differ between groups immunized with the same dose (FIG. 3D).

Figure 4A:
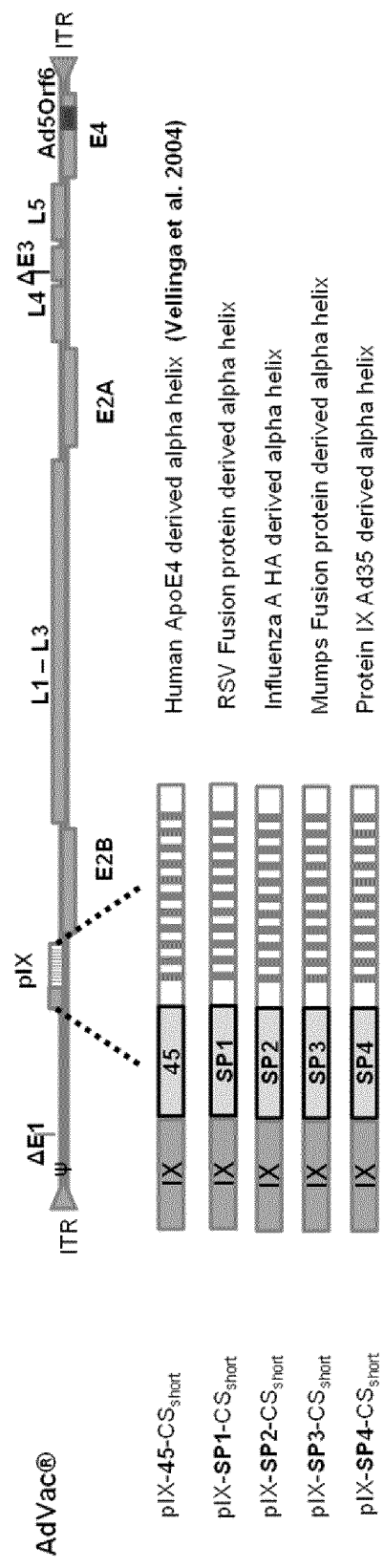
FIG. 4: Human ApoE4 based alpha-helix spacer replacement (A) Schematic representation of empty vectors encoding only CS$_{short}$ fused to pIX via four different viral-origin spacers (SP1-4) namely, alpha helixes from Respiratory Syncytial Virus (RSV) fusion protein (F-protein), Influenza A HA, Mumps F-protein and HAdV35 pIX$_{mod}$ compared to the previously described human ApoE4 based alpha-helix 45 Å-spacer (16). (B and C) Western blots showing the capsid incorporation efficiency of the CS$_{short}$ linked via different spacers (SP1-4). 1.5, 0.75 and 0.37×10¹⁰ VP/well of each spacer vector HAdV35. empty.pIX-SP1-CS$_{short}$, HAdV35.empty.pIX-SP2-CS$_{short}$, HAdV35.empty.pIX-SP3-CS$_{short}$ and HAdV35.empty.pIX-SP4-CS$_{short}$ directly compared to equal quantity of the native-pIX HAdV35.empty vector and the HAdV35.empty.pIX-45 Å-CS$_{short}$ vector. The blots are stained with anti-pIX (6740) monoclonal antibody and anti-fiber (4D2) as a loading control. (D) Shows a Western blot with 1.5, 0.5 and 0.16× 10¹⁰ VP/well of HAdV26.empty.pIX-SP1-CS$_{short}$, HAdV26.empty.pIX-45 Å-CS$_{short}$ and HAdV26.empty stained with anti-CS (2A10) to show the capsid incorporation of the pIX-SP1-CS$_{short}$ compared to the pIX-45 Å-CS$_{short}$.
Figure 4B:
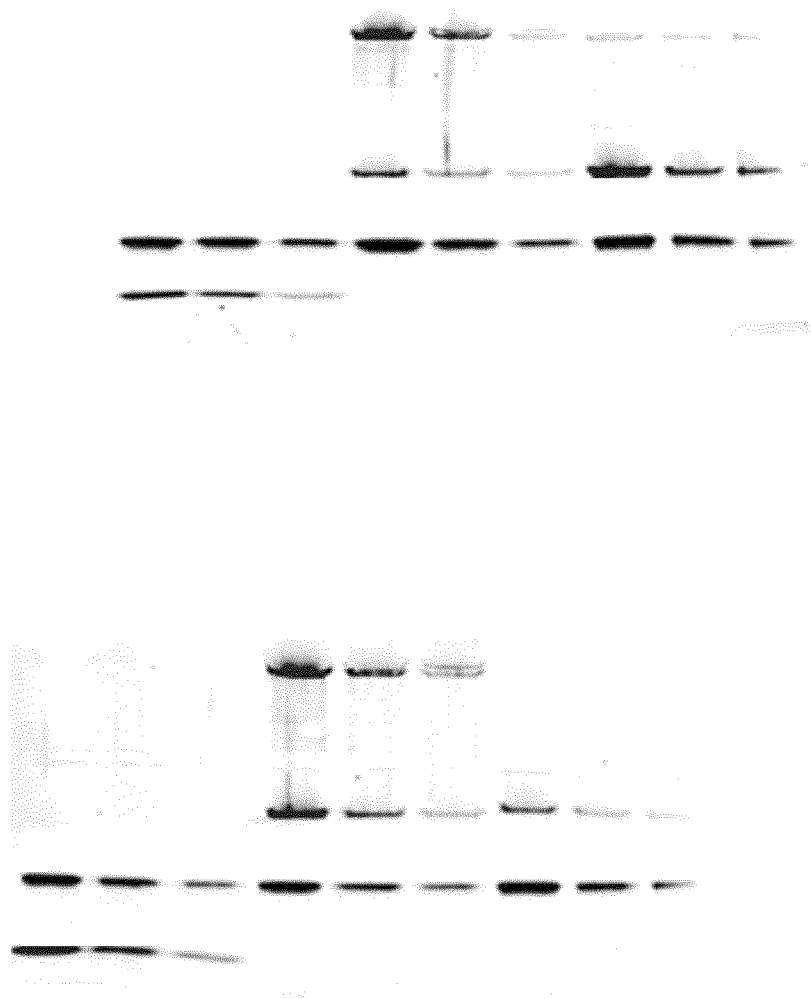
Figure 4C:
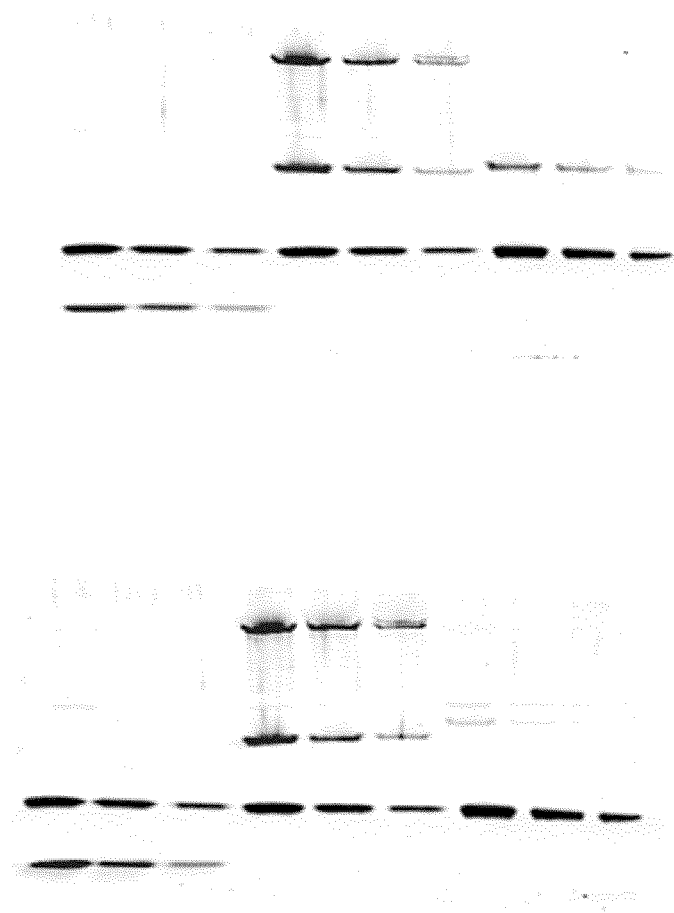
Figure 4D:

These results indicate that pIX-$CS_{short}$-modified vectors may result in a slight reduction of vector potency, but not in the absolute magnitude of the cellular responses that can be reached at higher dosing of the vector. Taken together, these results indicate that $CS_{short}$ display on pIX can be implemented on CS transgene-expressing HAdV35 vectors, significantly increasing humoral immune responses while maintaining strong cellular immune responses.

Replacement of the Alpha-Helical 45 Å-Spacer (From Human Origin) with the 45 Å Spacer SP1 (From Viral Origin)

To circumvent the potential unfavorable effects, in terms of autoimmune disease upon vaccination with the vectors containing the human origin 45-spacer, four biochemically similar spacers (SP1-SP4) from viral origin were designed (Table 4).

TABLE 4

Biochemical characteristics spacers

| Spacer | Sequence (a.a.) | Origin | Predicted secondary structure |
|---|---|---|---|
| 45A | ARLSKELQAAQARLGADMEDVCGRLVQYRGEDGA (34) | ApoE4 | Alpha-helix |
| SP1 | CNGTDAKIKLIKQELDKYKNAVTELQLLMQST (32) | RSV F | Alpha-helix |
| SP2 | TNEKFHQIEKEFSEVEGRIQDLEKYVEDTKIDL (33) | HA | Alpha-helix |
| SP3 | QTNARAIAAMKNSIQATNRAIFEVKEGTQQ (30) | Mumps F | Alpha-helix |
| SP4 | SSARDDKATAALAQADSATREANVVSQQALDA 32 | HAdV35p$IX_{mod}$ | Alpha-helix |

The following four spacer proteins from viral origin were tested in vitro: spacer 1 (SP1), a RSV Fusion protein comprising the amino acid sequence of SEQ ID NO:2; spacer 2 (SP2), an Influenza A HA comprising the amino acid sequence of SEQ ID NO:3; spacer 3 (SP3), a Mumps Fusion protein comprising the amino acid sequence of SEQ ID NO:4; and finally spacer 4 (SP4), a HAdV35.pIX fragment with point mutations comprises the amino acid sequence of SEQ ID NO:5.

HAdV35.empty vectors encoding the pIX-$CS_{short}$ with the four different spacers, SP1-4, HAdV35.empty.pIX-SP1-$CS_{short}$, HAdV35.empty.pIX-SP2-$CS_{short}$, HAdV35.empty.pIX-SP3-$CS_{short}$ and HAdV35.empty.pIX-SP4-$CS_{short}$ were generated as described above using the three plasmid system in PER.C6® cells (FIG. 4A and Table 1). The CsCl-purified vectors were tested in WB to determine the capsid incorporation efficiency of the four pIX proteins with the four different spacers. Three different concentrations of the SP1-4 vectors (1.5, 0.75 and $0.37\times10^{10}$ VP/well) were directly compared to the 45-spacer control vector and the native pIX in HAdV35.empty (FIG. 4B). Staining of the protein was performed with both, anti-pIX monoclonal and anti-CS (2A10) antibodies. Since the anti-pIX antibody recognizes one specific epitope in pIX HAdV35, in contrast to the 27-NANP repeat sequence for the anti-CS antibody (2A10), the anti-pIX antibody was considered to be more sensitive to the differences in capsid incorporation than the anti-CS NANP-repeat specific antibody. At equal loading (fiber band ~35 kDa) of the vectors, the pIX-SP1-CS$_{short}$ (~32 kDa) showed to be the most abundant in the capsid, compared to pIX-45-CSshort (~32 kDa) and pIX (~14 kDa). In terms of capsid incorporation, pIX-SP2-CS$_{short}$ was the second best followed by pIX-SP3-CS$_{short}$ and finally the pIX-SP4-CS$_{short}$ with the lowest capsid incorporated modified pIX. To confirm the application of SP1 as a functional spacer for pIX fusions, the same capsid modifications were generated in HAdV26, except for SP2. HAdV26.empty.pIX-SP1-CS$_{short}$, HAdV26.empty.pIX-SP3-CS$_{short}$ and HAdV26.empty.pIX-SP4-CS$_{short}$ were produced, as described earlier, with the whole genome plasmids in PER.C6® cells and characterized (Table 1). The indicated vectors were analyzed in WB by comparing three different concentrations (1.5, 0.5 and 0.16× $10^{10}$ VP/well) of the SP1, SP3 and SP4 to the control vector 45 spacer (FIG. 4D). Consistent with the results observed for the HAdV35 SP1-SP4 spacer vectors, the staining performed with anti-CS NRNP-repeat antibody 2A10 showed no difference in the capsid incorporation efficiency (unlike the staining with the anti-pIX antibody) (Table 3). In terms of capsid incorporation efficiency the SP1 spacer is comparable to the 45-spacer in HAdV35 and HAdV26 vectors. Slight differences are observed with the SP2 spacer and larger differences with the SP3 and SP4 in terms of capsid incorporation. This effect of the spacers on the observed capsid incorporation efficiency shows that the choice of the spacer is important. The differences observed in capsid incorporation efficiency with the SP2, SP3 and SP4 spacers in HAdV35 suggest that the choice of the alpha-helical spacer is important for efficient capsid incorporation.

Example 3

Manufacturability pIX-CS$_{short}$ Modified HAdV35 and HAdV26 Vectors

Kinetics and Propagation in PER. C6® cells of HAdV26 pIX Modified Vectors

Since many pathogens such as malaria causing parasite are often endemic to resource-limited areas, manufacturing processes with high yields are necessary to ensure proper vaccine coverage. Based on observations that some HAdV vectors can be sensitive to certain genetic modifications such as inserted transgenes, the relative viral particle increase (VP/ml) and the kinetics of the pIX modified vectors were assessed in suspension cultures of PER.C6® cells in parallel with control vectors known for their high and low producibility (i.e. 'good producers' and 'low producers'). The growth of the adenoviral vectors on PER.C6® cells (in suspension) in a bioreactor (data not shown) was performed to assess the relative VP/ml increase and the kinetics of these vectors. The assessment of adenovirus vector propagation on PER.C6® cells entails: the infection (n=3) of PER.C6® cells (10-15 ml 1×10$^6$ viable cells (vc/ml)) at a predetermined VP/cell ratio of either 70 or 900, the harvest (100 µl n=3) at 0, 1, 2, 3 and 4 days post infection (DPI) and the titer (VP/ml) determination by CMV promoter based VP-QPCR. Titer (VP/ml) Determination by CMV VP-QPCR In order to determine the VP/ml titers and the kinetics of pIX modified vectors in PER.C6® cells, cell lysis was performed by addition of 1% Triton™ X-100 (Sigma-Aldrich) followed by a treatment with DNase I (Roche) to remove the un-capsidated viral DNA in the solvent. After lysis the samples were diluted 1000× in H$_2$O (Gibco) and CMV based QPCR was performed. For the QPCR the forward primer (5'-TGGGCGGTAGGCGTGTA-3') and reverse primer (5'-CGATCTGACGGTTCACTAAACG-3') were used. The reactions were performed in triplicate in a final volume of 15 µl of which 5 µl of the diluted sample was mixed with 10 µl reaction mix. The reaction mix contained, in addition to 10 pmol primers and 2.5 pmol probe, 2× TaqMan Gene expression master mix (Life Technologies) and 25 mM MgCl$_2$. The final reaction was performed by denaturing the samples at 95° C. for 8 minutes, followed by 10 seconds at 95° C. and 30 seconds at 60° C. for 35 cycles in the QPCR machine (Applied Biosystems Viia7).

Figure 5A:
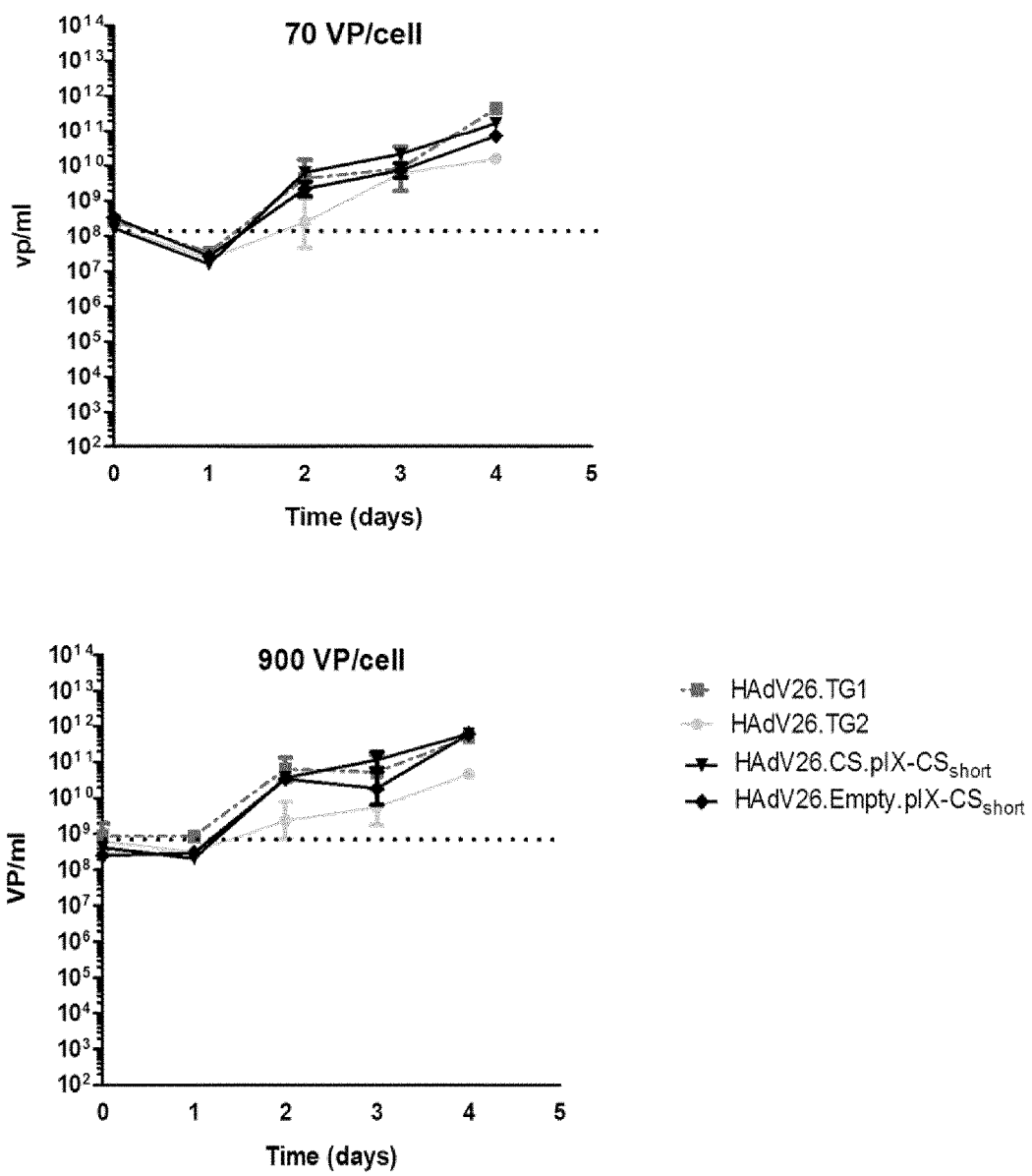
FIG. 5: Manufacturability of pIX-CS$_{short}$ modified vectors (A) Replication kinetics and the relative VP/ml increase (i.e. 'productivity') in time. 10 ml of suspension PER.C6® (sPER.C6®) cell culture is infected with HAdV26 vector at 70 and 900 VP/cell after which the culture is sampled in time (t=0, 1, 2, 3 and 4 days post infection (DPI)) (n=3) and analyzed with viral particles QPCR (VP-QPCR). The graphs show the kinetics and VP/ml increase of pIX-modified vectors (HAdV26.CS.pIX-CS$_{short}$ & HAdV26.empty.pIX-CS$_{short}$) compared to control vectors with high (HAdV26.TG1) and lower (HAdV26.TG2) yields in sPER.C6®. (B) Genetic stability assessment after extended passaging of pIX-modified batches in PER.C6® cells. The generation of batches entails upscaling in PER.C6® resulting in 6-7 viral passages (VPN7). To ensure genetically stable vectors, the purified batches are further passaged under controlled conditions, 70 or 900 VP/cell in 10 ml PER.C6® 3-4 passages (VPN 13-14) beyond the envisioned commercial scale (depending on the details of the process). The viral DNA is subsequently isolated and analyzed in pIX-PCR to determine genetic stability. (C) Representative Agarose gel pictures are shown of HAdV26.CS/Empty.pIX-CS$_{short}$ and HAdV35.CS/empty.pIX-CS$_{short}$ pIX-PCR at VPN 7 and VPN14 (passaged n=2). The positive (+) controls are the respective plasmid DNA constructs and the non-modified (−) pIX-native plasmid DNA along with PCR water (H₂O) control and the DNA marker (M).

The results show, a VP increase of approximately 2 Log when the cells are infected with 70 VP/cell, for the 'good' producer control and 1 Log for the 'low' producer control at day 3. Further increase in VP/ml titer is observed at day 4 for both (~1 log) (FIG. 5A, upper graph). The same relative increase as observed with the 70 VP/cell infections is also observed for the 'good' producer control (~2 Log) and the 'low' producer control (~1 Log) at day 3, when the cells were infected with 900 VP/cell (FIG. 5A, lower graph). The tested HAdV26.CS.pIX-CS$_{short}$ and rHHAdV26.empty.pIX-CS$_{short}$ vectors follow the same relative VP/ml increase, from time point 0 to day 4, as the 'good' producer control. This observation leads to the conclusion that pIX-CS$_{short}$ modification of the HAdV26 vectors with or without CS transgene in E1, does not affect the relative titer (VP/ml) increase in suspension PER.C6® cells.

Figure 5B:
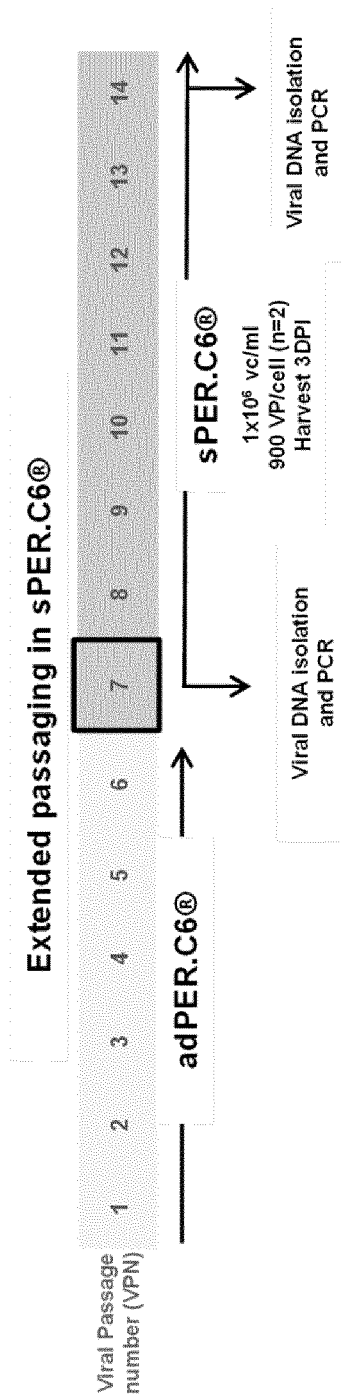

Genetic Stability pIX Modified Vectors After Extended Passaging in PER.C6® Cells As noted earlier, transgene products are produced during virus amplification in the E1-complementing PER.C6® cell line due to the highly potent CMV promoter. Depending on the transgene and perhaps the amount of expressed protein, this can be deleterious to virus formation. Since both the pIX-CS$_{short}$ and CS transgene are expressed in PER.C6® cells during virus propagation and upscaling we wanted to test whether these vectors remain genetically stable after extended passaging in PER.C6® cells. To determine the genetic stability of the pIX-CS$_{short}$ modified vectors with and without the CS transgene in E1 upon production in the producer PER.C6® cells, purified vectors were further propagated in PER.C6® up to four viral passages (VPN) beyond the envisioned commercial process (FIG. 5B gives a schematic representation of passaging adenovirus vectors in PER.C6® cells). Upon rescue and upscaling in PER.C6® cells, the vectors would have been passaged on average seven times prior to their purification with CsCl. During rescue the HAdV viral DNA is isolated to confirm the sequence of the pIX-CS$_{short}$ modification and E1 CS transgene (if applicable), by PCR and sequencing (Sanger). Further upscaling is executed with the vectors containing the correct pIX-CS$_{short}$ and E1 CS sequences. When purified, the viral DNA is isolated yet again and analyzed by PCR and confirmed by sequencing (Sanger). The subsequent passaging in PER.C6® cells (10 ml 1×10$^6$ VC/ml) is performed in controlled conditions by infecting the cells with either 70 or 900 VP/cell and harvesting at 3 DPI (n=2). Finally, at VPN 14 the viral DNA is isolated and analyzed by PCR.

pIX and E1 PCR Assay and Viral DNA Isolation

Figure 5C:
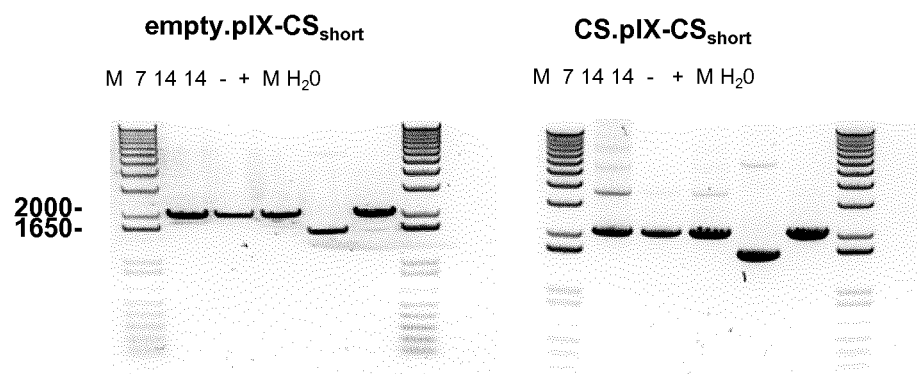
Figure 5C:
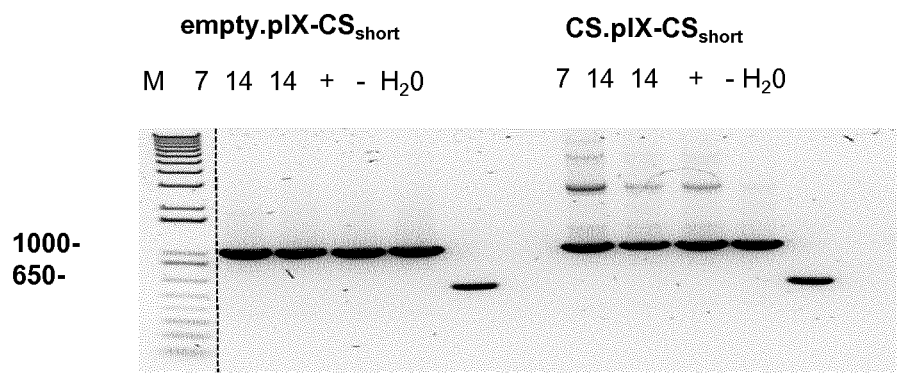

In order to assess whether the modified regions in the genome (i.e. pIX-CS$_{short}$ and the CS transgene) are still genetically encoded in the vector after extended passaging in PER.C6® cells, pIX and E1 specific PCR is performed on the viral DNA. Viral DNA from either crude lysates or purified vector batches was performed by using the GeneClean Spin kit (Bio101 Inc.) according to the manufacturer's recommendations. The DNA was subsequently used as a template to analyze pIX region and/or E1 region. For the HAdV26 pIX-PCR the primers (5'-GACATCAT-GAACGGGACTG-3' and 5'-GATCGAGATGCCGTA-GAG-3') and for the HAdV35 pIX-PCR the primers (5'-GGTGGGATTTTCAGATGGACAG-3' and 5'-CAGGGCATACCGTGCG-3') were used. The HAdV35 E1-PCR was performed with primers (5'-GGAGGTTTC-GATTACCGT-3' and 5'-CCCTCGATCTCGTATCATCA-3') and the HAdV26 E1-PCR with primers (5'-TGGCGC-GAAAACTGAATGAG-3' and 5'-GCAGGCGGGTTGT-CAAATAAG-3'). The HAdV35 and HAdV26 pIX-PCR conditions were as follows: 1 minute at 94° C., with 30 cycles of 94° C. for 30 seconds, 65° C. 30 seconds and elongation at 72° C. for 2 minutes. The HAdV35 and HAdV26 E1-PCR conditions were: 1 minute at 94° C., 10 cycles of 94° C. for 30 seconds, 62° C. 30 seconds (−0.5° C./cycle) and elongation at 72° C. for 2 minutes, followed by 20 cycles of 94° C. for 30 seconds, 57° C. 30 seconds and elongation at 72° C. for 2 minutes. All the reactions were performed with TaKara LA Taq (Clontech) according to manufacturer's recommendations. PIX-PCR Agarose gel analysis shows HAdV26.CS.pIX-$CS_{short}$, HAdV26.Empty.pIX-$CS_{short}$, HAdV35.CS.pIX-$CS_{short}$ and HAdV35.Empty.pIX-$CS_{short}$ at VPN 7 (preMVS) and VPN14 (FIG. 5C). Both the HAdV35 and HAdV26 pIX-$CS_{short}$ modified vectors, with or without the CS transgene in E1, are genetically stable after extended passaging in sPER.C6®, because only one band equivalent to the positive plasmid control is detected at VPN 7 and VPN14. The same analysis was performed on the E1-cassette with the E1-PCR on these vectors; the same observations were made as with the pIX-PCR, no additional bands besides the expected band were observed (data not shown). Taken together, this data suggests that upon production in suspension PER.C6® cells the pIX-$CS_{short}$ and E1 CS transgene in both the HAdV26 and HAdV35 vectors, remain genetically stable. In addition to the induction of superior CS-specific humoral responses, pIX-$CS_{short}$ modified vectors, with and without CS-transgene in E1, remain genetically stable and can be produced at high VP/ml titers in the E1-complementing PER.C6® cells platform. Considering that many of the pathogens which require a complex immune response are endemic to resource-limited areas, simplification of vaccine regimen and high manufacturing yields makes pIX-display technology particularly valuable to reach underserved communities most relying on vaccine coverage.

REFERENCES

1. Aide, P., C. Dobano, J. Sacarlal, J. J. Aponte, I. Mandomando, C. Guinovart, Q. Bassat, M. Renom, L. Puyol, E. Macete, E. Herreros, A. Leach, M. C. Dubois, M. A. Demoitie, M. Lievens, J. Vekemans, C. Loucq, W. R. Ballou, J. Cohen, and P. L. Alonso. Four year immunogenicity of the RTS,S/AS02(A) malaria vaccine in Mozambican children during a phase IIb trial. Vaccine 29:6059-6067.
2. Alonso, P. L., J. Sacarlal, J. J. Aponte, A. Leach, E. Macete, P. Aide, B. Sigauque, J. Milman, I. Mandomando, Q. Bassat, C. Guinovart, M. Espasa, S. Corachan, M. Lievens, M. M. Navia, M. C. Dubois, C. Menendez, F. Dubovsky, J. Cohen, R. Thompson, and W. R. Ballou. 2005. Duration of protection with RTS,S/AS02A malaria vaccine in prevention of Plasmodium falciparum disease in Mozambican children: single-blind extended follow-up of a randomised controlled trial. Lancet 366:2012-2018.
3. Alonso, P. L., J. Sacarlal, J. J. Aponte, A. Leach, E. Macete, J. Milman, I. Mandomando, B. Spiessens, C. Guinovart, M. Espasa, Q. Bassat, P. Aide, O. Ofori-Anyinam, M. M. Navia, S. Corachan, M. Ceuppens, M. C. Dubois, M. A. Demoitie, F. Dubovsky, C. Menendez, N. Tornieporth, W. R. Ballou, R. Thompson, and J. Cohen. 2004. Efficacy of the RTS,S/AS02A vaccine against Plasmodium falciparum infection and disease in young African children: randomised controlled trial. Lancet 364: 1411-1420.
4. Aponte, J. J., C. Menendez, D. Schellenberg, E. Kahigwa, H. Mshinda, P. Vountasou, M. Tanner, and P. L. Alonso. 2007. Age interactions in the development of naturally acquired immunity to Plasmodium falciparum and its clinical presentation. PLoS Med 4:e242.
5. Bojang, K. A., P. J. Milligan, M. Pinder, L. Vigneron, A. Alloueche, K. E. Kester, W. R. Ballou, D. J. Conway, W. H. Reece, P. Gothard, L. Yamuah, M. Delchambre, G. Voss, B. M. Greenwood, A. Hill, K. P. McAdam, N. Tornieporth, J. D. Cohen, and T. Doherty. 2001. Efficacy of RTS,S/AS02 malaria vaccine against Plasmodium falciparum infection in semi-immune adult men in The Gambia: a randomised trial. Lancet 358:1927-1934.
6. Havenga, M., R. Vogels, D. Zuijdgeest, K. Radosevic, S. Mueller, M. Sieuwerts, F. Weichold, I. Damen, J. Kaspers, A. Lemckert, M. van Meerendonk, R. van der Vlugt, L. Holterman, D. Hone, Y. Skeiky, R. Mintardjo, G. Gillissen, D. Barouch, J. Sadoff, and J. Goudsmit. 2006. Novel replication-incompetent adenoviral B-group vectors: high vector stability and yield in PER.C6 cells. The Journal of general virology 87:2135-2143.
7. Kester, K. E., J. F. Cummings, C. F. Ockenhouse, R. Nielsen, B. T. Hall, D. M. Gordon, R. J. Schwenk, U. Krzych, C. A. Holland, G. Richmond, M. G. Dowler, J. Williams, R. A. Wirtz, N. Tornieporth, L. Vigneron, M. Delchambre, M. A. Demoitie, W. R. Ballou, J. Cohen, and D. G. Heppner, Jr. 2008. Phase 2a trial of 0, 1, and 3 month and 0, 7, and 28 day immunization schedules of malaria vaccine RTS,S/AS02 in malaria-naive adults at the Walter Reed Army Institute of Research. Vaccine 26:2191-2202.
8. Kester, K. E., D. A. McKinney, N. Tornieporth, C. F. Ockenhouse, D. G. Heppner, T. Hall, U. Krzych, M. Delchambre, G. Voss, M. G. Dowler, J. Palensky, J. Wittes, J. Cohen, and W. R. Ballou. 2001. Efficacy of recombinant circumsporozoite protein vaccine regimens against experimental Plasmodium falciparum malaria. J Infect Dis 183:640-647.
9. Kester, K. E., D. A. McKinney, N. Tornieporth, C. F. Ockenhouse, D. G. Heppner, Jr., T. Hall, B. T. Wellde, K. White, P. Sun, R. Schwenk, U. Krzych, M. Delchambre, G. Voss, M. C. Dubois, R. A. Gasser, Jr., M. G. Dowler, M. O'Brien, J. Wittes, R. Wirtz, J. Cohen, and W. R. Ballou. 2007. A phase I/IIa safety, immunogenicity, and efficacy bridging randomized study of a two-dose regimen of liquid and lyophilized formulations of the candidate malaria vaccine RTS,S/AS02A in malaria-naive adults. Vaccine 25:5359-5366.
10. Ophorst, O. J., K. Radosevic, J. M. Klap, J. Sijtsma, G. Gillissen, R. Mintardjo, M. J. van Ooij, L. Holterman, A. Companjen, J. Goudsmit, and M. J. Havenga. 2007. Increased immunogenicity of recombinant HAdV35- based malaria vaccine through formulation with aluminium phosphate adjuvant. Vaccine 25:6501-6510.
11. Radosevic, K., A. Rodriguez, A. A. Lemckert, M. van der Meer, G. Gillissen, C. Warnar, R. von Eyben, M. G. Pau, and J. Goudsmit. 2011. The Th1 immune response to *Plasmodium falciparum* circumsporozoite protein is boosted by adenovirus vectors 35 and 26 with a homologous insert. Clin Vaccine Immunol 17:1687-1694.
12. Radosevic, K., C. W. Wieland, A. Rodriguez, G. J. Weverling, R. Mintardjo, G. Gillissen, R. Vogels, Y. A. Skeiky, D. M. Hone, J. C. Sadoff, T. van der Poll, M. Havenga, and J. Goudsmit. 2007. Protective immune responses to a recombinant adenovirus type 35 tuberculosis vaccine in two mouse strains: CD4 and CD8 T-cell epitope mapping and role of gamma interferon. Infect Immun 75:4105-4115.
13. Rodriguez, A., R. Mintardjo, D. Tax, G. Gillissen, J. Custers, M. G. Pau, J. Klap, S. Santra, H. Balachandran, N. L. Letvin, J. Goudsmit, and K. Radosevic. 2009. Evaluation of a prime-boost vaccine schedule with distinct adenovirus vectors against malaria in rhesus monkeys. Vaccine 27:6226-6233.
14. Shott, J. P., S. M. McGrath, M. G. Pau, J. H. Custers, O. Ophorst, M. A. Demoitie, M. C. Dubois, J. Komisar, M. Cobb, K. E. Kester, P. Dubois, J. Cohen, J. Goudsmit, D. G. Heppner, and V. A. Stewart. 2008. Adenovirus 5 and 35 vectors expressing *Plasmodium falciparum* circumsporozoite surface protein elicit potent antigen-specific cellular IFN-gamma and antibody responses in mice. Vaccine 26:2818-2823.
15. Stewart, V. A., S. M. McGrath, P. M. Dubois, M. G. Pau, P. Mettens, J. Shott, M. Cobb, J. R. Burge, D. Larson, L. A. Ware, M. A. Demoitie, G. J. Weverling, B. Bayat, J. H. Custers, M. C. Dubois, J. Cohen, J. Goudsmit, and D. G. Heppner, Jr. 2007. Priming with an adenovirus 35-circumsporozoite protein (CS) vaccine followed by RTS,S/AS01B boosting significantly improves immunogenicity to *Plasmodium falciparum* CS compared to that with either malaria vaccine alone. Infect Immun 75:2283-2290.
16. Vellinga, J., M. J. W. E. Rabelink, S. J. Cramer, D. J. M. Van der Wollenberg, H. Van der Meulen, K. N. Leppard, F. J. Fallaux, R. C. Hoeben. 2004. Spacers Increase the Accessibility of Peptide Ligands Linked to the Carboxyl Terminus of Adenovirus Minor Capsid Protein IX. Journal of Virology, April 2004, p. 3470-3479, Vol. 78, No. 7.

The invention claimed is:

1. A recombinant adenoviral vector comprising a nucleic acid encoding a capsid comprising a fusion protein consisting of a protein IX and a fragment of a circumsporozoite (CS) protein of *Plasmodium falciparum*, wherein said fragment comprises the amino acid sequence of SEQ ID NO:1.

2. The recombinant adenoviral vector according to claim 1, wherein said fusion protein comprises a linker located in between the pIX protein and the CS protein fragment.

3. The recombinant adenoviral vector according to claim 2, wherein the linker comprises an amino acid sequence having 2 to 15 consecutive flexible residues of glycine and/or serine.

4. The recombinant adenoviral vector according to claim 1, wherein said fusion protein comprises a spacer, located in between the pIX protein and the CS protein fragment.

5. The recombinant adenoviral vector according to claim 4, wherein said spacer comprises the amino acid sequence of SEQ ID NO:2.

6. The recombinant adenoviral vector according to claim 4, wherein said spacer comprises the amino acid sequence of SEQ ID NO:3.

7. The recombinant viral vector according to claim 1, wherein said vector further comprises a nucleic acid encoding one or more heterologous protein as a transgene.

8. The recombinant adenoviral vector according to claim 1, wherein said adenovirus is derived from a serotype selected from the group consisting of: HAdV4, HAdV5, HAdV11, HAdV26, HAdV35, HAdV48, HAdV49, HAdV50 non-human primate vectors and chimeric vectors.

9. A pharmaceutical composition comprising the recombinant adenoviral vector of claim 1 and a pharmaceutically acceptable carrier.

10. The pharmaceutical composition of claim 9, further comprising one or more adjuvants.

11. A method of treating a subject in need thereof, comprising administering to the subject the pharmaceutical composition of claim 9.

12. The method of claim 11, wherein the adenovirus is administered at a dose of $1 \times 10^7$ viral particles to $1 \times 10^{12}$ viral particles.

13. The method of claim 12, wherein the method further comprises administering to the subject a booster vaccine one week to one year after first administration.

14. The method of claim 13, wherein the booster vaccine comprises a different vector from the first administration.

15. An isolated host cell comprising the recombinant adenoviral vector of claim 1.

16. A method of producing the recombinant adenoviral vector of claim 1, comprising growing the isolated host cell comprising the recombinant adenoviral vector under conditions for the production of the recombinant adenovirus vector.

* * * * *

SEQUENCE LISTING

<160> NUMBER OF SEQ ID NOS: 24

<210> SEQ ID NO 1
<211> LENGTH: 151
<212> TYPE: PRT
<213> ORGANISM: Artificial Sequence
<220> FEATURE:
<223> OTHER INFORMATION: CS Short

<400> SEQUENCE: 1

```
Gly Asn Pro Asp Pro Asn Ala Asn Pro Asn Val Asp Pro Asn Ala Asn
1               5                   10                  15

Pro Asn Val Asp Pro Asn Ala Asn Pro Asn Val Asp Pro Asn Ala Asn
                20                  25                  30

Pro Asn Ala Asn Pro Asn Ala Asn Pro Asn Ala Asn Pro Asn Ala Asn
            35                  40                  45

Pro Asn Ala Asn Pro Asn Ala Asn Pro Asn Ala Asn Pro Asn Ala Asn
        50                  55                  60

Pro Asn Ala Asn Pro Asn Ala Asn Pro Asn Val Asp Pro Asn Ala Asn
65                  70                  75                  80

Pro Asn Ala Asn Pro Asn Ala Asn Pro Asn Ala Asn Pro Asn Ala Asn
                85                  90                  95

Pro Asn Ala Asn Pro Asn Ala Asn Pro Asn Ala Asn Pro Asn Ala Asn
            100                 105                 110

Pro Asn Ala Asn Pro Asn Ala Asn Pro Asn Ala Asn Pro Asn Ala Asn
        115                 120                 125

Pro Asn Ala Asn Pro Asn Ala Asn Pro Asn Ala Asn
    130                 135                 140

Lys Asn Asn Gln Gly Asn Gly
145                 150
```

<210> SEQ ID NO 2
<211> LENGTH: 32
<212> TYPE: PRT
<213> ORGANISM: Artificial Sequence
<220> FEATURE:
<223> OTHER INFORMATION: SP1 Spacer -continued

```
<400> SEQUENCE: 2

Cys Asn Gly Thr Asp Ala Lys Ile Lys Leu Ile Lys Gln Glu Leu Asp
1               5                   10                  15

Lys Tyr Lys Asn Ala Val Thr Glu Leu Gln Leu Leu Met Gln Ser Thr
            20                  25                  30

<210> SEQ ID NO 3
<211> LENGTH: 33
<212> TYPE: PRT
<213> ORGANISM: Artificial Sequence
<220> FEATURE:
<223> OTHER INFORMATION: SP2

<400> SEQUENCE: 3

Thr Asn Glu Lys Phe His Gln Ile Glu Lys Glu Phe Ser Glu Val Glu
1               5                   10                  15

Gly Arg Ile Gln Asp Leu Glu Lys Tyr Val Glu Asp Thr Lys Ile Asp
            20                  25                  30

Leu

<210> SEQ ID NO 4
<211> LENGTH: 30
<212> TYPE: PRT
<213> ORGANISM: Artificial Sequence
<220> FEATURE:
<223> OTHER INFORMATION: SP3 Spacer

<400> SEQUENCE: 4

Gln Thr Asn Ala Arg Ala Ile Ala Ala Met Lys Asn Ser Ile Gln Ala
1               5                   10                  15

Thr Asn Arg Ala Ile Phe Glu Val Lys Glu Gly Thr Gln Gln
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: SP4 Spacer

<400> SEQUENCE: 5

Ser Ser Ala Arg Asp Asp Lys Ala Thr Ala Leu Ala Gln Ala Asp
1               5                   10                  15

Ser Ala Thr Arg Glu Ala Asn Val Val Ser Gln Gln Ala Leu Asp Ala
            20                  25                  30

<210> SEQ ID NO 6
<211> LENGTH: 139
<212> TYPE: PRT
<213> ORGANISM: Artificial Sequence
<220> FEATURE:
<223> OTHER INFORMATION: HAdV-35 pIX

<400> SEQUENCE: 6

Met Ser Gly Asn Ala Ser Phe Lys Gly Gly Val Phe Ser Pro Tyr Leu
1               5                   10                  15

Thr Gly Arg Leu Pro Ser Trp Ala Gly Val Arg Gln Asn Val Met Gly
            20                  25                  30

Ser Thr Val Asp Gly Arg Pro Val Gln Pro Ala Asn Ser Ser Thr Leu
        35                  40                  45

Thr Tyr Ala Thr Leu Ser Ser Ser Pro Leu Asp Ala Ala Ala Ala Ala
```

```
            50                  55                  60
Ala Ala Ser Val Ala Ala Asn Thr Val Leu Gly Met Gly Tyr Tyr
 65                  70                  75                  80

Gly Ser Ile Val Ala Asn Ser Thr Ser Ser Asn Asn Pro Ser Thr Leu
                 85                  90                  95

Thr Gln Asp Lys Leu Leu Val Leu Leu Ala Gln Leu Glu Ala Leu Thr
                100                 105                 110

Gln Arg Leu Gly Glu Leu Ser Gln Gln Val Ala Glu Leu Arg Val Gln
                115                 120                 125

Thr Glu Ser Ala Val Gly Thr Ala Lys Ser Lys
            130                 135

<210> SEQ ID NO 7
<211> LENGTH: 134
<212> TYPE: PRT
<213> ORGANISM: Artificial Sequence
<220> FEATURE:
<223> OTHER INFORMATION: HAdV-26 pIX

<400> SEQUENCE: 7

Met Asn Gly Thr Gly Gly Ala Phe Glu Gly Gly Leu Phe Ser Pro Tyr
  1               5                  10                  15

Leu Thr Thr Arg Leu Pro Gly Trp Ala Gly Val Arg Gln Asn Val Met
                 20                  25                  30

Gly Ser Thr Val Asp Gly Arg Pro Val Leu Pro Ala Asn Ser Ser Thr
                 35                  40                  45

Met Thr Tyr Ala Thr Val Gly Asn Ser Ser Leu Asp Ser Thr Ala Ala
 50                  55                  60

Ala Ala Ala Ala Ala Ala Met Thr Ala Thr Arg Leu Ala Ser Ser
 65                  70                  75                  80

Tyr Met Pro Ser Ser Gly Ser Ser Pro Ser Val Pro Ser Ser Ile Ile
                 85                  90                  95

Ala Glu Glu Lys Leu Leu Ala Leu Leu Ala Glu Leu Glu Ala Leu Ser
                100                 105                 110

Arg Gln Leu Ala Ala Leu Thr Gln Gln Val Ser Glu Leu Arg Glu Gln
                115                 120                 125

Gln Gln Gln Gln Asn Lys
            130

<210> SEQ ID NO 8
<211> LENGTH: 376
<212> TYPE: PRT
<213> ORGANISM: Artificial Sequence
<220> FEATURE:
<223> OTHER INFORMATION: P. falciparum circumsporozoite (CS) protein

<400> SEQUENCE: 8

Lys Leu Ala Thr Met Met Arg Lys Leu Ala Ile Leu Ser Val Ser Ser
  1               5                  10                  15

Phe Leu Phe Val Glu Ala Leu Phe Gln Glu Tyr Gln Cys Tyr Gly Ser
                 20                  25                  30

Ser Ser Asn Thr Arg Val Leu Asn Glu Leu Asn Tyr Asp Asn Ala Gly
                 35                  40                  45

Thr Asn Leu Tyr Asn Glu Leu Glu Met Asn Tyr Tyr Gly Lys Gln Glu
 50                  55                  60

Asn Trp Tyr Ser Leu Lys Lys Asn Ser Arg Ser Leu Gly Glu Asn Asp
 65                  70                  75                  80
```

```
Asp Gly Asn Asn Asn Asn Gly Asp Asn Gly Arg Glu Gly Lys Asp Glu
            85                  90                  95

Asp Lys Arg Asp Gly Asn Asn Glu Asp Asn Glu Lys Leu Arg Lys Pro
        100                 105                 110

Lys His Lys Lys Leu Lys Gln Pro Ala Asp Gly Asn Pro Asp Pro Asn
        115                 120                 125

Ala Asn Pro Asn Val Asp Pro Asn Ala Asn Pro Asn Val Asp Pro Asn
        130                 135                 140

Ala Asn Pro Asn Val Asp Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
        165                 170                 175

Ala Asn Pro Asn Ala Asn Pro Asn Ala Asn Pro Asn Ala Asn Pro Asn
        180                 185                 190

Ala Asn Pro Asn Val Asp Pro Asn Ala Asn Pro Asn Ala Asn Pro Asn
        195                 200                 205

Ala Asn Pro Asn Ala Asn Pro Asn Ala Asn Pro Asn Ala Asn Pro Asn
        210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
        245                 250                 255

Ala Asn Pro Asn Ala Asn Pro Asn Ala Asn Lys Asn Asn Gln Gly Asn
        260                 265                 270

Gly Gln Gly His Asn Met Pro Asn Asp Pro Asn Arg Asn Val Asp Glu
        275                 280                 285

Asn Ala Asn Ala Asn Ser Ala Val Lys Asn Asn Asn Asn Glu Glu Pro
        290                 295                 300

Ser Asp Lys His Ile Lys Glu Tyr Leu Asn Lys Ile Gln Asn Ser Leu
305                 310                 315                 320

Ser Thr Glu Trp Ser Pro Cys Ser Val Thr Cys Gly Asn Gly Ile Gln
        325                 330                 335

Val Arg Ile Lys Pro Gly Ser Ala Asn Lys Pro Lys Asp Glu Leu Asp
        340                 345                 350

Tyr Ala Asn Asp Ile Glu Lys Lys Ile Cys Lys Met Glu Lys Cys Ser
        355                 360                 365

Ser Val Phe Asn Val Val Asn Ser
        370                 375

<210> SEQ ID NO 9
<211> LENGTH: 9
<212> TYPE: PRT
<213> ORGANISM: Artificial Sequence
<220> FEATURE:
<223> OTHER INFORMATION: HAdV35 hexon epitope

<400> SEQUENCE: 9

Lys Tyr Thr Pro Ser Asn Val Thr Leu
1               5

<210> SEQ ID NO 10
<211> LENGTH: 4
<212> TYPE: PRT
<213> ORGANISM: Artificial Sequence
<220> FEATURE:
<223> OTHER INFORMATION: NANP-repeat

<400> SEQUENCE: 10
```

Asn Ala Asn Pro
1

<210> SEQ ID NO 11
<211> LENGTH: 8
<212> TYPE: PRT
<213> ORGANISM: Artificial Sequence
<220> FEATURE:
<223> OTHER INFORMATION: Middle linker

<400> SEQUENCE: 11

Gly Gly Ser Gly Gly Gly Ser Gly
1               5

<210> SEQ ID NO 12
<211> LENGTH: 9
<212> TYPE: PRT
<213> ORGANISM: Artificial Sequence
<220> FEATURE:
<223> OTHER INFORMATION: immunodominant CS epitope

<400> SEQUENCE: 12

Asn Tyr Asp Asn Ala Gly Thr Asn Leu
1               5

<210> SEQ ID NO 13
<211> LENGTH: 9
<212> TYPE: PRT
<213> ORGANISM: Artificial Sequence
<220> FEATURE:
<223> OTHER INFORMATION: immunodominant hexon epitope

<400> SEQUENCE: 13

Lys Tyr Thr Pro Ser Asn Val Thr Leu
1               5

<210> SEQ ID NO 14
<211> LENGTH: 34
<212> TYPE: PRT
<213> ORGANISM: Artificial Sequence
<220> FEATURE:
<223> OTHER INFORMATION: 45A Spacer

<400> SEQUENCE: 14

Ala Arg Leu Ser Lys Glu Leu Gln Ala Ala Gln Ala Arg Leu Gly Ala
1               5                   10                  15

Asp Met Glu Asp Val Cys Gly Arg Leu Val Gln Tyr Arg Gly Glu Asp
            20                  25                  30

Gly Ala

<210> SEQ ID NO 15
<211> LENGTH: 17
<212> TYPE: DNA
<213> ORGANISM: Artificial Sequence
<220> FEATURE:
<223> OTHER INFORMATION: Primer 1

<400> SEQUENCE: 15
tgggcggtag gcgtgta                                                  17

<210> SEQ ID NO 16
<211> LENGTH: 22
<212> TYPE: DNA
<213> ORGANISM: Artificial Sequence
<220> FEATURE:

<223> OTHER INFORMATION: Primer 2

<400> SEQUENCE: 16
cgatctgacg gttcactaaa cg                                              22

<210> SEQ ID NO 17
<211> LENGTH: 19
<212> TYPE: DNA
<213> ORGANISM: Artificial Sequence
<220> FEATURE:
<223> OTHER INFORMATION: Primer 3

<400> SEQUENCE: 17
gacatcatga acgggactg                                                  19

<210> SEQ ID NO 18
<211> LENGTH: 18
<212> TYPE: DNA
<213> ORGANISM: Artificial Sequence
<220> FEATURE:
<223> OTHER INFORMATION: Primer 4

<400> SEQUENCE: 18
gatcgagatg ccgtagag                                                   18

<210> SEQ ID NO 19
<211> LENGTH: 22
<212> TYPE: DNA
<213> ORGANISM: Artificial Sequence
<220> FEATURE:
<223> OTHER INFORMATION: Primer 5

<400> SEQUENCE: 19
ggtgggattt tcagatggac ag                                              22

<210> SEQ ID NO 20
<211> LENGTH: 16
<212> TYPE: DNA
<213> ORGANISM: Artificial Sequence
<220> FEATURE:
<223> OTHER INFORMATION: Primer 6

<400> SEQUENCE: 20
cagggcatac cgtgcg                                                     16

<210> SEQ ID NO 21
<211> LENGTH: 18
<212> TYPE: DNA
<213> ORGANISM: Artificial Sequence
<220> FEATURE:
<223> OTHER INFORMATION: Primer 7

<400> SEQUENCE: 21
ggaggtttcg attaccgt                                                   18

<210> SEQ ID NO 22
<211> LENGTH: 20
<212> TYPE: DNA
<213> ORGANISM: Artificial Sequence
<220> FEATURE:
<223> OTHER INFORMATION: Primer 8

<400> SEQUENCE: 22
ccctcgatct cgtatcatca                                                 20

```
<210> SEQ ID NO 23
<211> LENGTH: 20
<212> TYPE: DNA
<213> ORGANISM: Artificial Sequence
<220> FEATURE:
<223> OTHER INFORMATION: Primer 9

<400> SEQUENCE: 23
tggcgcgaaa actgaatgag                                               20

<210> SEQ ID NO 24
<211> LENGTH: 21
<212> TYPE: DNA
<213> ORGANISM: Artificial Sequence
<220> FEATURE:
<223> OTHER INFORMATION: Primer 10

<400> SEQUENCE: 24
gcaggcgggt tgtcaaataa g                                             21
```